United States Patent [19]

Sarr

[11] Patent Number: 4,470,122
[45] Date of Patent: Sep. 4, 1984

[54] INTEGRATED ELECTRO-OPTICAL POSITION SENSING, WORKPIECE PROBING AND DISPLAY METHOD AND APPARATUS

[75] Inventor: Dennis P. Sarr, Kent, Wash.
[73] Assignee: The Boeing Company, Seattle, Wash.
[21] Appl. No.: 306,952
[22] Filed: Sep. 30, 1981
[51] Int. Cl.³ ............................................... G01B 7/34
[52] U.S. Cl. ..................................... 364/559; 73/621; 364/507; 364/551
[58] Field of Search ........ 364/507, 518, 520, 550–552, 364/559, 474; 73/618, 621; 356/138, 141; 382/43

[56] References Cited

U.S. PATENT DOCUMENTS

| | | | |
|---|---|---|---|
| 3,571,579 | 3/1971 | Whitehouse et al. | 364/507 |
| 3,913,387 | 10/1975 | Sasaki et al. | 73/621 |
| 3,996,792 | 12/1976 | Kubota et al. | 364/507 |
| 4,092,867 | 6/1978 | Matzuk | 73/621 |
| 4,282,577 | 8/1981 | Abend et al. | 364/507 |

*Primary Examiner*—Errol A. Krass
*Attorney, Agent, or Firm*—Christensen, O'Connor, Johnson & Kindness

[57] ABSTRACT

A system is disclosed for automatically correlating the position of a nondestructive test (NDT) probe and the magnitude of a probe produced NDT signal as the probe is moved manually, and independently of any mechanical constraint, over a planar surface of a test workpiece. The probe position is sensed electro-optically by a position-determining subsystem including an LED light source affixed to the probe housing so as to be movable therewith and a scanning assembly on which are mounted spaced apart, scanning light sensors, sensor drive motors and angle encoders. An associated control circuit provided in part by a programmed microcomputer is interfaced with the sensors, drive motors and angle encoders of the scanning assembly such that as the electro-optical sensors scan through the position of the LED light source on the probe, peak sensory signals are produced and the corresponding, instantaneous scan angles are registered by the angle encoders and are fed into the microcomputer which, using triangulation processes, determines the position of the probe in the probed area and produces signals representing the coordinates of such instantaneous probe position. Concurrently therewith, the magnitude of the NDT probe signal is registered, correlated and stored in memory along with the probe position coordinates. A video display subsystem, including display control circuitry, also provided by a programmed microcomputer, receives the position coordinate signals and the correlated NDT signal and processes these signals for display on a cathode ray tube (CRT) so as to present a C-scan video display of the NDT signal magnitude as a function of position on the workpiece in the area traversed by the probe.

17 Claims, 38 Drawing Figures

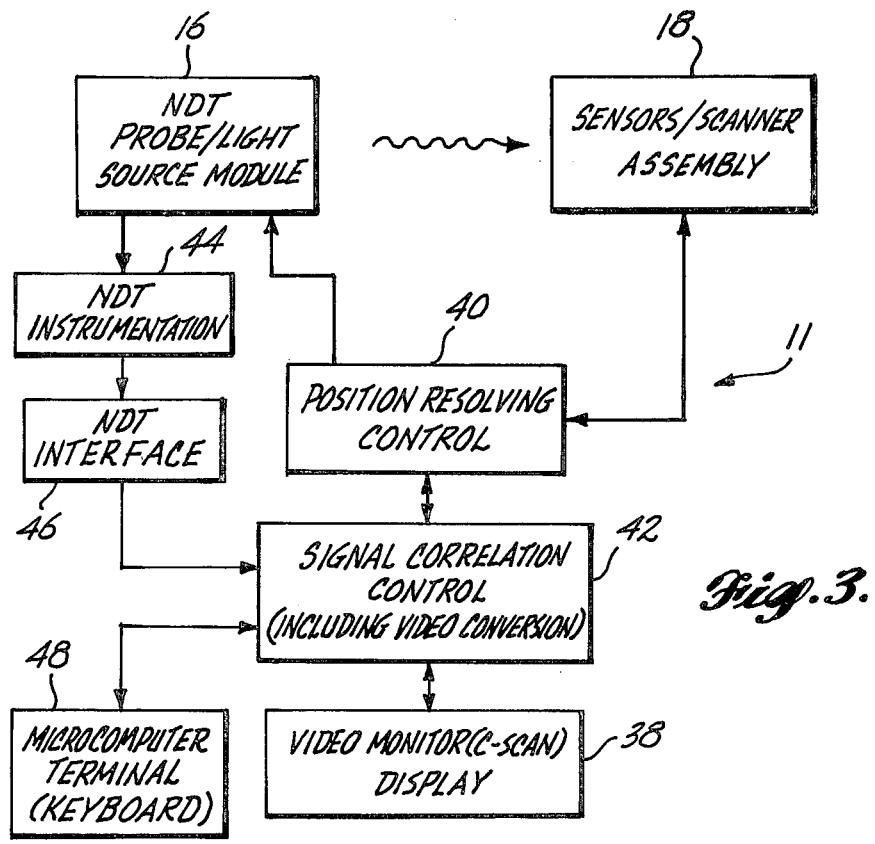
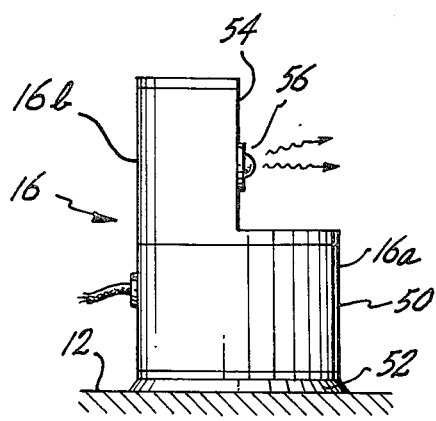
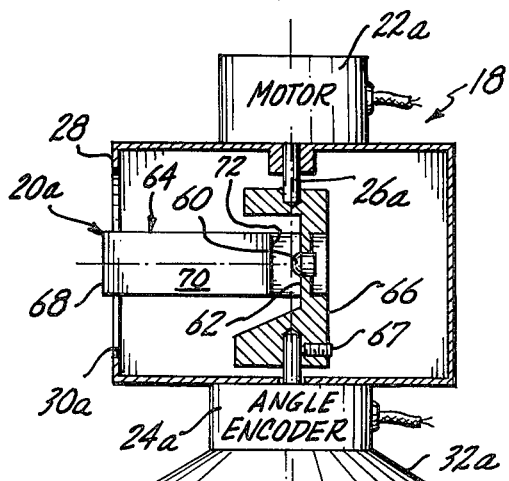

Fig. 7. VIDEO DISPLAY 38

*Fig. 10c.* CONTROL COMMANDS ENTERED AT TERMINAL 48

A     SELECTS AN ANALOG TO DIGITAL TEST, THIS IS A CONTINUOUS LOOPING PROGRAM SAMPLING THE ANALOG SIGNAL AND DISPLAYING IT'S HEXADECIMAL VALUE ONTO THE CRT SCREEN, OPERATION IS TERMINATED BY 'X' ON CRT TERMINAL.

N     THIS IS A TEST THAT OBTAINS AN ANALOG SIGNAL FOR 4 msec, DIGITIZES THE SIGNAL AND STORES IT AS PEAK & Z. IT IS USED IN THE QUANTIZE SUBROUTINE.

PXX    THIS SELECTS THE PIXEL RESOLUTION PER X,Y, POINT FOR SCAN DISPLAY. IF PIXEL AND RSTN = 0 THEN THE BLOCK IS 2X2 DOTS, IF PIXEL & RSTN = 1 THEN THE BLOCK IS 4X4 DOTS  ENTER SELECTED RESOLUTION IN HEXADECIMAL BYTE XX AFTER 'P'

/XX    THIS SELECTS A SCALE FACTOR FOR THE VIDEO SCREEN. NORMALLY THE X AND Y BINARY NUMBER REPRESENTS 1/100 INCH. FOR EXAMPLE /0A WOULD RESULT WITH EACH GRAPHICS DOT EACH 0.10 INCH. ENTER SELECTED RESOLUTION IN HEXADECIMAL BYTE XX AFTER '/'

Fig.10d. CONT. CONTROL COMMANDS

1    SELECTS A SLOW SCAN MODE FOR THE POSITION SENSOR, ENABLES GRAPHICS DISPLAY OF X & Y COORDINATE WITH THE QUANTIZED NDI INSTRUMENT AS ITS Z AXIS. OPERATION IS TERMINATED BY 'X' ON CRT TERMINAL

2    SELECTS A FAST SCAN MODE (ie NO SOFTWARE TIME DELAYS) WITH OPERATIONAL FEATURES SIMILAR TO '1'

3    SELECT = A SMALL SCAN MODE WITH OPERATIONAL FEATURES SIMILAR TO '2'

4    THIS CLEARS THE VIDEO SCREEN AND REINITIALIZES 'N', 'P', '/' TO ØFFH, Ø, Ø1H RESPECTIVELY.

5    SELECTS CONTINUATION OF THE PREVIOUS MODE OF OPERATION PREVIOUS MODE IS INITIALIZED TO BE 'Z'

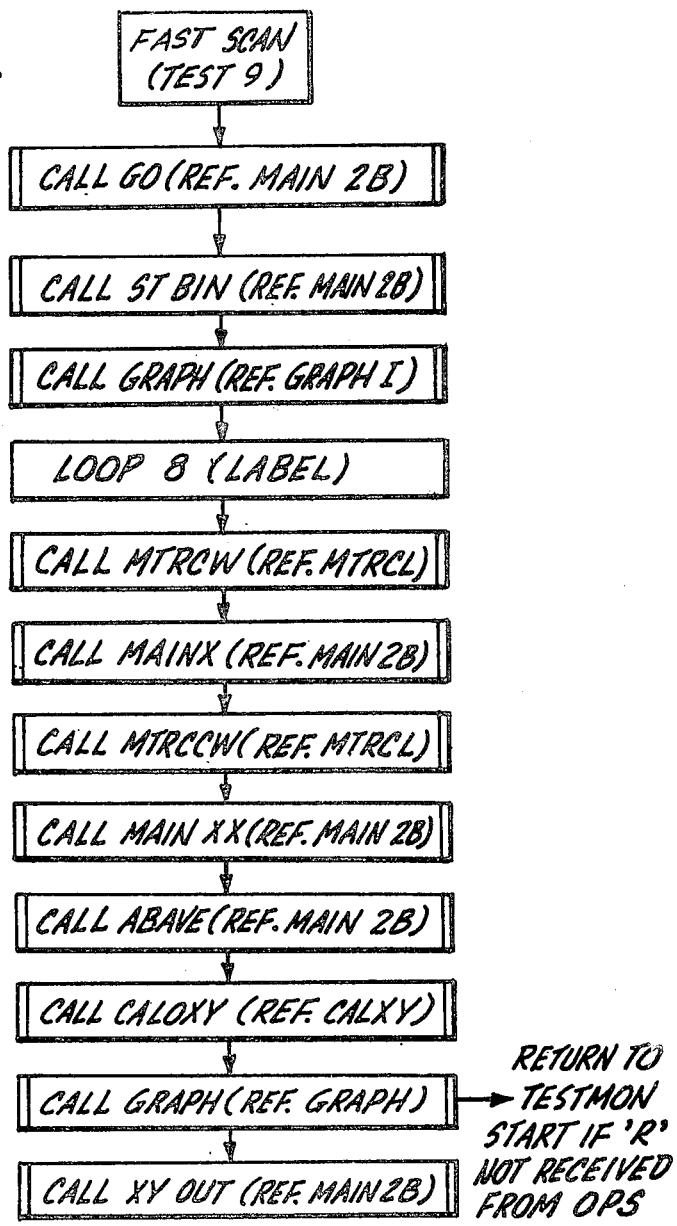

Fig. 15a. *GENERAL SUBROUTINES USED IN TESTS 8, 9 & 10*

GO: INITIALIZES CONTROL 40 BY SETTING I/O PORTS 90 TO OUTPUT MODE, AND CAUSES ALL ZEROS TO BE DISPLAYED ON X, Y COORD. DISPLAY 92

STBIN: SETS I/O PORTS 86 TO STROBED INPUT MODE SO AS TO LATCH DATA FROM SHAFT ENCODERS (24a) AND COUNTERS (74a)

ANGIN: SETS I/O PORTS 86 TO REGULAR (NON-STROBED) INPUT MODE FOR READING ANGLE ENCODERS (24a) AND COUNTERS (74b)

GRAPHI: VIDEO GRAPHICS INITIALIZATION FOR PREPARING VIDEO DISPLAY 38 FOR RECEIVING VIDEO DATA; FOUR 'U' IN ASCII ARE TRANSMITTED TO DISPLAY 38

MTRCW: MOVES $\alpha$ & $\beta$ MOTORS (22a, 22b) CW AND CCW RESPECTIVELY FOR 80 INCREMENTS MTRCCW: MOVES $\alpha$ & $\beta$ MOTORS (22a, 22b) CCW AND CC RESPECTIVELY FOR 80 INCREMENTS

*Fig. 15b.* (CONT. GEN: SUBROUTINES USED IN TESTS 8, 9 & 10)

MAIN X: READ IN $\alpha$ & $\beta$ COUNTS FROM ENCODERS (24a) AND COUNTERS (74a) AND STORE RESULTS IN AAVE & BAVE RESPTIVELY (SEE BELOW)

MAIN XX: SAME AS MAIN X EXCEPT STORE RESULTS IN CAVE & DAVE RESPECTIVELY (SEE BELOW)

ABAVE: AVERAGES ANGLES $\alpha$ & $\beta$ FROM MEMORY LOCATIONS RAVE & BAVE FOR $\alpha$, AND LOCATIONS CAVE & DAVE FOR $\beta$ & STORES RESULTING AVERAGES AS PEAK ah, PEAK al, PEAK bh, & PEAK bl (SEE FIGS 16a, b AND THE OPERATIONS AND LABELS REFERRED TO THEREIN INCLUDING:
AAVE
BAVE
CAVE
DAVE
ACHK
BCHK
ANGHEX CALCXY: CALCULATE X & Y POSITION COORD. FROM $\alpha$ & $\beta$ ACCORDING TO —
$$Y = \frac{\sin\alpha \sin\beta}{\sin\delta}, \quad X = \frac{d \sin\alpha \sin(90° - \beta)}{\sin\delta}$$
WHERE $\delta = (180° - (\alpha + \beta))$
$d$ = DISTANCE BETWEEN SENSORS
(SEE FIG. 17 AND OPERATIONS AAAAH & XXYY USED THEREIN)

*Fig. 15c.* (CONT. GEN. SUBROUTINES USED IN TESTS 8, 9 & 10)

GRAPH: TRANSMITS X, Y POSITION COORDINATES TO VIDEO PROCESSING SECTION OF CONTROL 42, TRANSMISSION IS BY AN ASCII S FOLLOWED BY X-LSB (LEAST SIGNIFICANT BITS), X-MSB (MOST SIGNIF. BITS), Y-LSB & Y-MSB. ROUTINE WAITS FOR A RECEIVED 'R' (ASCII) IN ORDER TO CONT. TEST MODE, AND IF AN 'R' IS NOT RECEIVED, THIS ROUTINE TRANSMITS AN ASCII X AND CALLS TSTMON ROUTINE FOR NEW EXECUTION MODE

XYOUT: CONVERTS X, Y POSITION DATA IN HEX (XHEX AND YHEX) BINARY TO DECIMAL (BASE 10) AND CAUSES THE DECIMAL VALUE TO BE DISPLAYED ON DISPLAY 42

WAIT: A DELAY OPERATION CAUSING A WAITING INTERVAL BETWEEN SUCESSIVE SCANS OF SENSORS 20a & 20b OPERATIVE DURING SLOW SCAN TEST 8

*Fig. 19a.* SPECIAL SUBROUTINES USED IN TEST 10 (SMALL SCAN)

CNT FLG : A FLAG THAT IS SET TO EITHER 0 FOR THE INITIAL LARGE SCAN PHASE OF TEST 10 OR TO '0FFH FOR THE REPEATING SMALL SCAN PHASE OF TEST 10

COUNT : COUNTS NUMBER OF SMALL SCAN DITHERS BETWEEN CALLING UP ZABSUP & ZAB FOR ZEROING $\alpha$ & $\beta$ SENSORS 20a & 20b CWSET : MOVES $\alpha$ & $\beta$ SENSORS ACCORDING TO COUNTS DEVELOPED IN CWCNT (SEE BELOW) BY CALLING ACWAB (SEE BELOW); RESULTS IN MOVING SENSORS THROUGH A SMALL SCAN DITHER PASSED THE LAST PEAK ANGLE OF MODULE 16 PLUS 15°. (SEE FIGURE 20)

CWCNT : CALCULATES COUNTS FOR EXECUTING CWSET, ABOVE, BY DEVELOPING A VALUE $I$ = REQUIRED CW STEPS FOR $\alpha$ AND $J$ = REQUIRED CCW STEPS FOR $\beta$ WHERE $I$ & $J$ ARE TO BE USED IN ACWAB & ACCWAB (DESCRIBED BELOW) (SEE FIGURE 22)

*Fig.19e.* (CONT. SPECIAL SUBROUTINES USED IN TEST 10 SMALL SCAN))

CCWSET: PROVIDES FOR MOVING SENSORS A FIXED NUMBER OF STEPS CORRESPONDING TO APPROX. 30° IN OPPOSITE DIRECTION TO CWSET FOR COMPLETING REMAINING HALF-CYCLE OF SMALL SCAN DITHER BY CALLING UP ACCWAB (SEE FIG. 21)

ACWAB: EXECUTES JOINT AND SEPARATE MOVEMENTS OF $\alpha$ & $\beta$ SENSORS ACCORDING TO CWSET USING I, J VALUES (SEE CWCNT ABOVE) AND CWAL - STEPS $\alpha$ SENSOR CW ONE STEP; CCWAL - STEPS $\alpha$ SENSOR CCW ONE STEP; AND SO FORTH FOR CWBE & CCWBE. (SEE FIG. 23)

ACCWAB: COUNTERPART OF ACWAB FOR MOVEMENT OF SENSORS IN OPPOSITE DIRECTION IN RESPONSE TO I & J VALUES (SEE FIG. 24)

*Fig. 19c.* (CONT. SPECIAL SUBROUTINES USED IN TEST 10 (SMALL SCAN))

ZABSUB: A TRANSITION ROUTINE CONNECTING THE SMALL SCAN TEST 10 ROUTINE TO THE ZERO $\alpha, \beta$ ROUTINE ZAB DESCRIBED BELOW (SEE FIGURE 25)

ZAB: CALLED UPON ONCE EVERY 10 SMALL SCAN DITHER CYCLES TO ZERO THE $\alpha$ & $\beta$ SENSORS 20a & 20b. (SEE FIGS. 26a, b)

INTEGRATED ELECTRO-OPTICAL POSITION SENSING, WORKPIECE PROBING AND DISPLAY METHOD AND APPARATUS

BACKGROUND OF THE INVENTION

The invention relates to systems for probing test objects and automatically monitoring the probe position of the object, such as in non-destructive testing (NDT) of structures in which an electrical test signal is produced representing some characteristic of the object, and variations in the test signal are correlated with different probe positions.

While the invention has a broad range of applications, it is particularly useful in the NDT field. Often in non-destructive testing, there is a need to provide a record of probed-for test signals as a function of probe position. For example, in ultrasonic NDT systems, an ultrasonic transducer probe is mounted on a mechanical linkage that allows the probe to be movable in a constrained pattern over a test structure. Position transducers are associated with the mechanical linkage and produce electrical signals representing the instantaneous position of the probe in relation to the test structure. The ultrasonic transducer in the probe produces variable test signals related to a particular characteristic of the test structure and such signal variations can be recorded as a function of the probe position signals.

However, the mechanical linkage that is commonly used to generate the probe position signals has a number of drawbacks, especially in certain test environments. For example, when the test structure and the inspection area thereon are relatively large, mechanical linkage systems lack the flexibility and scale needed to scan large areas. The testing of aircraft skins is one example of a test environment presenting the above-noted difficulties. The orientation and relatively large surface expanse of test areas on the aircraft skin are generally incompatible with the use of mechanical linkage assemblies. Also, the lack of portability of most mechanical linkage systems, particularly in systems that are capable of testing a relatively large surface area, is a further shortcoming.

The inherent nature of mechanical linkage, particularly when constructed to span relatively large test areas, has severe practical limitations in providing a suitably high level of position resolution. When an NDT probe is connected to the mechanical linkage, often unwanted constraints result, limiting the operator's independent control over movement of the probe from position to position.

Additionally, existing NDT systems of this general type do not provide an effective presentation of the probed-for test data. As a result, the data developed by such systems are difficult to analyze, increasing the possibility of the operator overlooking significant structural faults.

Accordingly, it is an object of the invention to provide in a method and apparatus of the above-described type, improvements that are characterized by an overall greater flexibility and ease in independently positioning and moving the probe, while still developing data representing the probe signal as a function as probe position. Related objects include system portability, enhanced resolution and self-referencing of the monitored probe position.

Another object of the invention is to provide a correlated probe signal and probe position method and apparatus having the above-characterized capabilities and further providing that the probe NDT signal and probe position data are correlated and displayed in a manner that facilitates rapid assimilation and interpretation of the test results.

SUMMARY OF THE INVENTION

As disclosed more fully herein, method and apparatus are provided for electro-optically locating an independently movable module that incorporates both a test probe and a position-identifying light (or other radiation) source, developing coordinate signals representing the module position, and receiving, storing and correlating such position coordinate signals with a test signal produced by the test probe. The test signal represents certain predetermined characteristics of a probe object, such as in ultrasonic NDT probing of a test workpiece. The stored position and test signal information is then retrieved and displayed as a multi-dimensional representation of the variable level test signal as a function of probe position relative to the test object.

Preferably, the method and apparatus comprise a video signal processing means and associated video (CRT) display means for converting the stored, correlated position and test signal data into a C-scan video display of the probed characteristics of the object. Such video processing means incorporates means for quantizing the test signal according to variations in its level and displaying discrete level changes as different video impressions, such as relative darkening on a nominally lighter screen background, or color encoding of the quantized signal levels.

The electro-optical position locating preferably comprises apparatus for automatic scanning by a plurality of directional light sensors. Such sensors are carried on a portable scanner assembly that can be removably mounted adjacent a surface area of the test object, such as on a surface of an aircraft body near the area that is to be probed. In this preferred form, a scan control is provided as a subsystem of the position determining control for controlling the scan rates and angles of the scanning operations. This scan control includes signal processing and control for automatically referencing the sensor scan angles to the location of the scanner assembly, which in turn is mounted at a predetermined position relative to the particular surface area that is the object of the test. In this manner, the electro-optical scanning for the position of the probe light source module is precisely and automatically referenced to a prescribed surface area on the test object so that a permanent record can be made of the test results.

To provide a complete disclosure of the invention, reference is made to the appended drawings and following description of one particular and preferred embodiment.

BRIEF DESCRIPTION OF THE DRAWINGS

FIG. 3 is a generalized block diagram of the method and apparatus of the invention.

FIG. 4 is an enlarged, elevational view of the probe/light source module referred to above in the brief description of FIG. 2.

FIG. 5 is an enlarged, elevational view of one of the light sensors, drive motors and angle encoder subassemblies of the electro-optical scanner assembly referred to above in connection with FIG. 2.

FIGS. 8-26 are a series of flow charts of the programming of microcomputers incorporated in the position resolving and signal correlation controls of the block diagram shown in FIG. 3.

DETAILED DESCRIPTION

Figure 1:
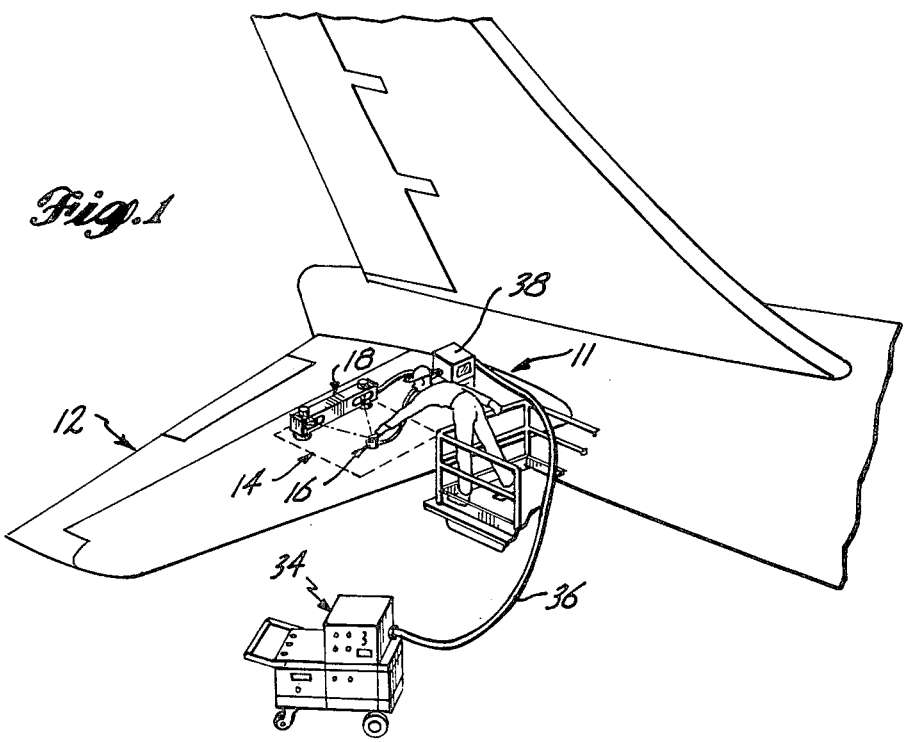
FIG. 1 is a perspective view of the integrated workpiece probing, probe position sensing and display method and apparatus depicted in a test situation in which an operator is probing a preselected surface area on the tail section of an aircraft.
Figure 2:
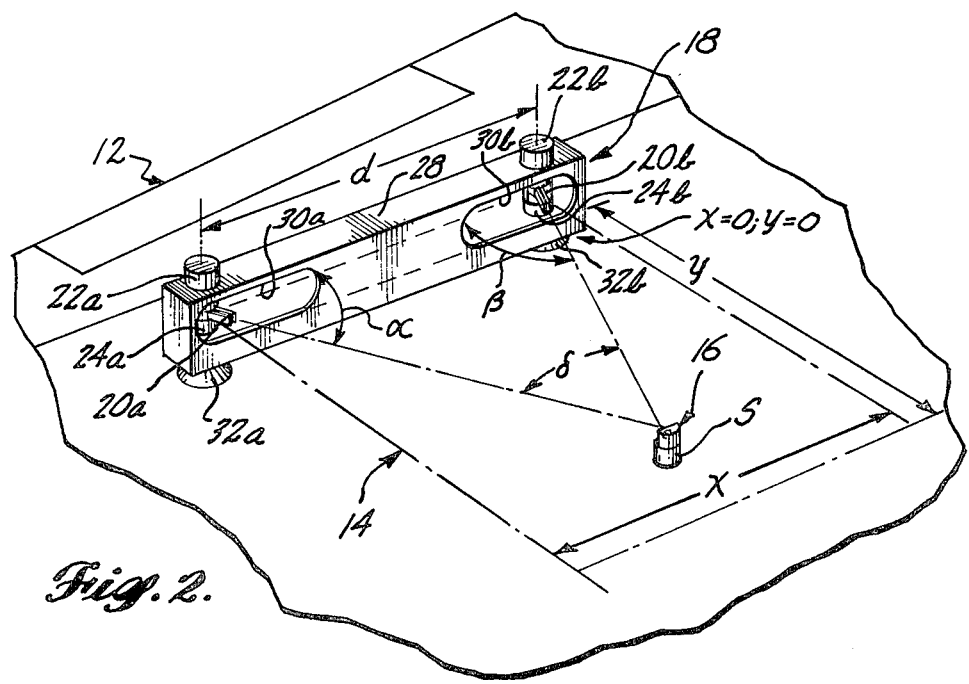
FIG. 2 is an enlarged, detailed view of a portable, electro-optical scanner assembly and an associated probe/light source module constituting elements of the probing, position sensing and display method and apparatus of the invention.

With reference to FIGS. 1 and 2, a preferred embodiment of the integrated workpiece probing, probe position sensing and display system 11 is shown in use for nondestructive testing (NDT) of a flat area on an aircraft's tail section 12. A predefined area 14 of the tail section is scanned by a probe/light source module 16, including an NDT ultrasonic transducer, to develop a variable level test signal related to predetermined characteristics of the material and/or structure being probed. Tail section 12 is, in this case, comprised of a composite of fiber reinforced resin materials and ultrasonic NDT is especially effective in inspecting such synthetic composites for structural flaws. Module 16 also incorporates a light (or other short wave radiation) source, such as an LED, for indicating the location of module 16 at any instance. The point of origin of this source of light is tracked by an assembly 18 of scanning electro-optical sensors 20a and 20b. An assembly 18 is portable and can be removably attached to the workpiece surface that is to be inspected, as illustrated by the mounting of assembly 18 on the upper elevator surface of tail section 12. Sensors 20a and 20b are scanned in reciprocating, arcuate scanning paths oriented to scan across the position of module 16 in a rectangular test area 14 adjacent assembly 18.

By using a scanning arc for each of sensors 20a and 20b of somewhat greater than 90°, swinging from inwardly confronting positions in which the instantaneous scan angles $\alpha$ and $\beta$ are zero and hence aligned with the lengthwise dimension of assembly 18, to positions in which angles $\alpha$ and $\beta$ are somewhat greater than 90°, a scanning area 14 of generally rectangular shape is defined in which one side of area 14 lies along with length of assembly 18. Sensors 20a and 20b develop in conjunction with other control circuitry, sensed angles $\alpha_p$ and $\beta_p$, at which instant sensors 20a and 20b are aligned with the light source on module 16. This angle information ($\alpha_p$ and $\beta_p$), together with a predetermined distance d along a baseline separating the axes of sensors 20a and 20b, enable determination of the position of module 16 by means of control circuitry described hereinafter. The computed position of module 16 is represented by rectangular coordinates, including an X value (corresponding to the dimension of area 14 parallel to baseline d), and a Y value (corresponding to the dimension of area 14 lying orthogonally to baseline d). A reference point in area 14 in which both X and Y equal zero is established at the corner of area 14 adjacent to sensor 20a, as indicated in FIG. 2.

For driving sensors 20a and 20b, assembly 18 includes drive motors 22a and 22b, respectively, and associated angle encoders 24a and 24b, respectively, wherein each associated set of a sensor, drive motor and angle encoder is connected to a common vertically journalled shaft as illustrated by shaft 26a in FIG. 5. A hollow, elongate support housing 28 of rectangular cross-section, mounts each sensor, drive motor and angle encoder subassembly, and such subassemblies are disposed at opposite ends of housing 28 and arranged so that the common drive shafts, e.g., shaft 26a as shown in FIG. 5, extend downwardly through the interior of housing 28. Sensor windows 30a and 30b are provided as shown in FIG. 2, elongated along the lengthwise dimension of housing 28 and positioned so as to be in general registration with the arcuate scanning movements of sensors 20a and 20b, respectively. For removably attaching assembly 18 to the workpiece surface, such as tail section 12, suction cups 32a and 32b are provided, with the nonsuction mounting end permanently affixed to the bottom wall of housing 28 as depicted in FIG. 5.

Figure 6:
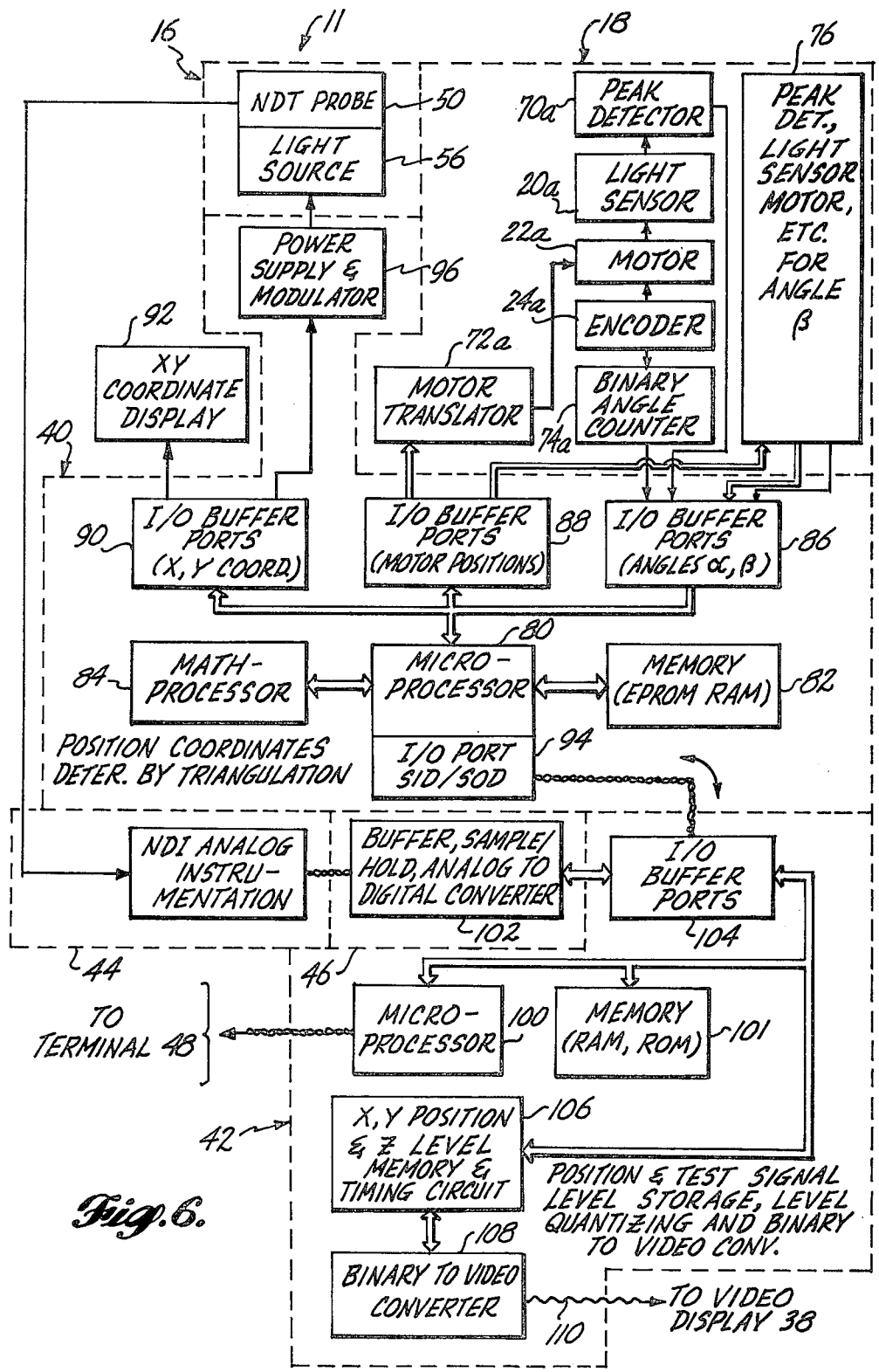
FIG. 6 is a detailed, comprehensive block diagram of the integrated probing, position sensing and display method and apparatus shown more generally in the block diagram of FIG. 3.

The control circuitry which is associated with module 16 and assembly 18, and which is described more fully below in connection with FIGS. 3 and 6, is contained in a portable control unit 34 that communicates via a cable 36 with module 16, assembly 18 and a portable, video display 38. Control unit 34 receives signal information representing the coordinates X and Y of the position of module 16, along with a variable level probed-for ultra-sonic test signal representing some predetermined characteristic of the structure of tail section 12. These signals are correlated and processed so as to be presented on display 38 in a C-scan format depicting the probed-for test characteristics as a function of X,Y position in the two-dimensional test area 14.

With reference to FIG. 3, probe/light source module 16 and sensor/scanner 18 are connected to the following control circuitry. Signals representing the angle information ($\alpha$ and $\beta$) are connected to a position resolving control 40 which in turn is coupled to a signal correlation control 42. Controls 40 and 42 incorporate circuitry for performing the principal signal processing of the system, and as described more fully hereinafter, each control preferably includes a microprocessor-based computer.

The NDT signal from the probe portion of module 16 is coupled to NDT instrumentation circuit 44 which cofunctions with the ultrasonic probe of module 16 to develop an analog probe signal in a manner known per se. The analog output from instrumentation circuit 44 is further processed by an NDT interface circuit 46 which converts the signal from analog-to-digital form. This digitized signal is applied to an input port of signal correlation control 42 which also receives signal information from control 40 representing the instant position of module 16. The probe level and position signals are stored in a correlated fashion available for subsequent retrieval in response to operator commands entered via a microcomputer terminal 48, including a keyboard, which as depicted in FIG. 3, is coupled to control 42. In the preferred form of control 42, the correlated signal information is processed by video conversion circuitry for conditioning the signals so as to be presented on video display 38, such as provided by a CRT, in the format of a C-scan in which the level of the probe test signal is represented by varying video signals on the screen, such as relative darker spots on a light background, and the corresponding position information is represented by the location of the image on the two dimensional screen. In this embodiment, the X coordinates of area 14 (FIG. 2) are oriented along the horizontal axis of the screen of display 38 while the Y coordinates correspond to the screen's vertical dimension. The result is a persistent display in two dimensions, namely the X and Y screen positions of a third dimension, namely, the signal level, Z, of the test probe. Such a format is commonly called a C-scan display.

With reference to FIG. 4, module 16 may be of any suitable configuration for housing an NDT probe and mounting a light or other radiation source. Here an ultrasonic probe 50 is encapsulated in an upstanding cylindrical housing 16a forming a lower portion of module 16. Probe 50 has an active transducer face 52 formed at its bottom which is acoustically coupled to the test object's surface in a manner known per se in the field of ultrasonic nondestructive testing. An upper portion of module 16 is shaped in the form of a half cylinder structure 16b in which the diametrical face 54 supports source 56 and is elevated from and at right angles to the workpiece plane so it can be rotated into light coupling relationship with sensors 20a and 20b of assembly 18. Source 56 is provided in this embodiment by a pn gallium arsenide infrared LED operated at a relatively high power output, such as 150 milli-watts at a wavelength of 0.93 micrometers. While the particular shape of module 16 is not critical it should be configured so as to be easily held in the operator's hand for movement over the workpiece surface while maintaining light source 56 oriented toward the baseline d of scanner assembly 18 (see FIG. 2).

Sensors 20a and 20b are identical, and with reference to FIG. 5, sensor 20a is shown to incorporate a light sensitive transducer 60, such as provided by a photodiode having spectral sensitivity matching source 56. Transducer 60 is mounted on an interior wall 62 of a light channeling shroud 64. Transducer 60 is mounted on an interior wall 62 of a light channeling shroud 64. An integral sleeve portion 66 of shroud 64 is fixed coaxially on shaft 26a and secured thereto by a set screw 67. Portion 66 supports an elongated, vertically and lengthwise slotted light channeling shroud portion 68 that projects radially from shaft 26a and sleeve 66 toward the direction of test area 14 and module 16 therewithin (see FIG. 2). Shroud portion 68 is formed with a black anodization to minimize light reflection. Slot 70, which may for example be 0.030 inches wide, extends in length from the radially outermost terminus of portion 68, inwardly toward sleeve 66 where it (slot 70) opens into an enlarged transducer mounting cavity 72, which in part is bounded by wall 62 on which transducer 60 is mounted in alignment with slot 70. Thus, transducer 60 receives light that is channeled rearwardly through the slot 70 of shroud portion 68 so that as sensors 20a scans in a horizontal plane across the point of light emission by source 56, transducer 60 receives a burst of light stimulation, and in response thereto produces a rising then falling electrical signal that is then peak detected and used to store the associated, instantaneous angle $\alpha_p$. The sensor 20b and its associated components similarly produce a signal that is effective to register an instantaneous angle $\beta_p$.

With reference to the more detailed block diagram of system 11 shown in FIG. 6, sensor/scanner assembly 18 additionally includes a peak detector 70a, a binary angle counter 74a, and a motor translator 72a, all associated with sensor 20a. A corresponding set of components are associated with sensor 20b as indicated by block 76. Peak detector 70a is electrically connected to the leads of sensor 20a for detecting the occurence of a peak light receiving event by transducer 60 (FIG. 5); motor translator 72a receives binary signal information from control 40 and drives motor 22a in a controlled scanning motion; and binary angle counter 74a also associated with sensor 20a; registers the angular position of the sensor in response to pulse signals representing incremental rotation that are received from bidirectional angle encoder 24a. Motors 22a and 22b are stepper motors and cooperate in a known manner with suitably phased pulse train signals received from the motor translator 72a, and a like translator (not shown) for stepper motor 22b, so as to be driven incrementally in steps in either direction and with sufficient step-wise rapidity to cause sensors 20a and 20b to appear to move smoothly through predetermined scanning arcs. Encoder 24a and its counterpart associated with sensor 20b have a relatively high resolution such as 0.025 angle degrees to enable a correspondingly high resolution of the X,Y position coordinates. The coincidence of output signals developed by peak detector 70a and binary angle counter 74a, together generate the value of the angle $\alpha_p$ which is fed to control 40. The output signal information from block 76 defining the angle $\beta_p$ is generated in a like manner and is also applied to control 40.

A power supply 96 drives the LED light source 56. Supply 96 may be provided with a modulator for modulating the supply voltage for LED source 56 at a preselected frequency, such as 30 kilohertz, and in such case tuned circuits are provided in the peak detection networks 70a, 76 matching the modulation frequency in order to enhance the signal-to-noise ratio in the electro-optical coupling between source 56 and the light sensors 20a and 20b.

Control 40 is implemented by a microprocessor based computer including a microprocessor 80, an associated memory 82 and a math processor 84. Signal information is received by and transmitted from control 40 by means of a plurality of input/output (I/O) ports indicated in FIG. 6 as I/O buffer ports 86 for receiving the $\alpha$ and $\beta$ angle information from sensor/scanner assembly 18 and I/O buffer ports 88 for feeding the scan control signals from control 40 to motor translator 72a associated with sensor 20a and to a like motor translator (not separately shown) associated with light sensor 20b. The X,Y coordinate values are computed by microprocessor 80, memory 82 and math processor 84, using a triangulation computation process known per se, and the resulting X and Y values are transmitted from control 40 via I/O buffer ports 90 to an auxiliary X,Y coordinate display 92, and via an I/O port 94 to signal correlation control 42 for coprocessing with the variable level NDT probe signal from probe 50 of module 16. In this embodiment, microprocessor 80 is provided by an 8085 eight-byte central processing unit, such as commercially available from Intel Corporation of Santa Clara, Calif. and the associated components are also commercially available as follows: memory (EPROM, RAM) 82; math processor 84-AM9511 processor; I/O buffer ports 86—8155 RAM with I/O and timer; Intel; buffer ports 88 and 90—8255 programmable peripheral interfaces, Intel;

and I/O port 94—available as serial output pins SID & SOD on the 8085 CPU, Intel. The foregoing components of control 40 may alternatively be obtained as a package from Intel under their system designation SDK-85 modified with expansion circuitry.

Control 42 is implemented, as shown in FIG. 6, by a second microprocessor based computer, which in conjuction with associated digital circuitry correlates the variable level NDT probe signal Z with the probe position X,Y coordinates developed by control 40. For this purpose, control 42 includes a microprocessor 100, an associated memory 101 which has a RAM and a ROM for both scratch pad and non-volatile memory capability, I/O buffer ports 104, X,Y position and Z level memory and timing circuit 106 and binary to video converter 108. Microprocessor 100 may be provided by an 8085 by Intel Corporation, or processor 100 together with memory 101 may be purchased as a package together with a compatible memory and timing circuit 106 as DOSC MIB-85 from Digitron Optical Scanning Corp., New York, N.Y.

The NDT probe signal is sampled and converted to digital form by buffer and interface circuit 46, which includes a sample/hold and analog-to-digital converter circuit 102 and thence the digitized NDT signal Z is applied via I/O buffer ports 104 to microprocessor 100 and memory 101 for processing thereby. Buffer ports 104 also provide an input interfacing for receiving the X,Y position coordinates from port 94 of control 40.

The X,Y position information along with the test signal level Z is processed, while in binary form, by microprocessor 100 operates in response to a control program, described more fully hereinafter, stored in a ROM section of memory 101 and the resulting, correlated X, Y and Z data is then stored in memory and timing circuit 106 which has sufficient memory capacity for semipermanently storing the position coordinates and associated test probe level for each resolved point on the preselected test area 14 of the probed structure. The test signal Z is also quantized into eight discrete levels, depending on its amplitude, and the thusly quantized level data is also stored in circuit 106. For presentation on video display 38, binary to video converter 108 receives the binary X, Y and Z data from circuit 106 and converts same to a variable level video (analog) signal that appears on output lead 110 and is fed to the CRT drive circuitry of display 38. Lead 110 may be a standardized video output suitable for driving most conventional CRT displays in which the video information is synchronized, like a television raster, with interlaced video fields.

Memory and timing circuit 106 is provided by a memory-mapped video subsystem, available commercially as video boards SVB-80 from Digitron Optical Scanning Corp., supra. Such video boards are compatible with the above-mentioned DOSC MIB-85 available from the same company, and include a set of three identical memory boards, each having two separate 16,384 byte memory sections and associated timing circuitry for generating memory address signals for each of two interlaced video fields at an output strobing rate that is synchronized with the video raster. Each of the three identical memory boards includes a unique X,Y address for each X,Y position resolved by the position determining control 40. Depending upon the quantized Z level received from microprocessor 100 and memory 101, the three boards store ones and zeroes for each X,Y position to collectively form a three-bit binary word representing 8 discrete video levels, related to the magnitude of the test signal Z.

Thus, for any given X,Y position, memory and timing circuit 106 will store and relinquish when called upon, video signal level in binary that changes in eight discrete steps, depending on the magnitude of the variable Z level developed by the test probe. The resulting presentation on video display 38 is that of a grey scale, in which the lightest portions of the screen represent minimum Z levels while the darkest portions of the screen represent maximum Z levels and the discrete grey levels therebetween represent intermediate values of the test signal Z. To enable an operator to quickly determine what sections he has already scanned in area 14 (see FIG. 2), the scaling provided by circuit 106 is designed to provide a minimum grey level noticeably greyer than the nominally lighter background on the video screen for each X,Y position that has been traversed by probe 16 in area 14.

Memory and timing circuit 106 is configured so as to receive X,Y position addresses and correlated probe level Z, at random times. Such data is, however, stored in circuit 160 in a non-random, memory-mapped format and is outputed to binary to video converter 108 in a predetermined sequence for synchronizing the data with the video raster of display 38.

Figure 7:
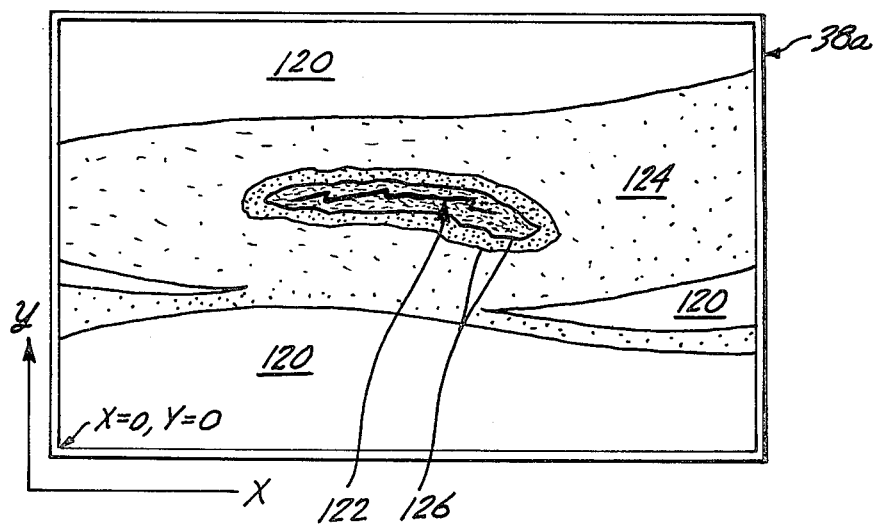
FIG. 7 depicts, diagrammatically, an example of a video display of a fault characteristic in a probed workpiece surface scanned by the probe/light source module referred to above in connection with FIGS. 2 and 4.

An example of how probed-for test information, developed by the system 11, is displayed is shown in FIG. 7 in which a video representation of the test area 14 (FIG. 2) is presented on screen 38a of display 38. The X and Y axes of area 14 correspond to the horizontal and vertical dimensions, respectively, of screen 38a. The video impression on screen 38a varies with incrementally changing levels of grey, from a relatively light background 120, corresponding to regions of area 14 which have not been traversed by the operator's movement of module 16 (FIG. 2), to a maximum darkness indicated by arrow 122 where the variable level of the probe test signal Z is at a maximum. Intermediate levels of the grey scaling include a minimum grey level, indicated at 124, corresponding to levels of test signal Z below that of any significance. Grey level 124 is distinguished from the lighter background region 120 so as to indicate to the operator that the region 124 has been traversed by module 16 and a test signal has been developed for that section of area 14. As the test signal Z increases in amplitude, the quantization of the Z signal by control 42 as described above, produces discretely increasing grey (relatively darker) levels as shown by contour lines 126 surrounding the darkest section 122 indicating that as the probe is moved in proximity to the area 122, the test signal Z is increasing in amplitude. The relatively darker regions 122 and 126 in the scanned area 124, may represent a fault or other aberration in the otherwise homogenous composition of tail section 12 in test area 14 (see FIGS. 1 and 2). After a section of area 14 has been scanned, and the correlated probe signal levels Z for that region are stored in circuit 106 (FIG. 6), such data is updated each time the operator rescans the same section of area 14, with the revised Z level, if changed, being stored in circuit 106 and displayed on screen 38a. Thus, memory and timing circuit 106 serves as a semi-permanent memory or storage of the X,Y position and correlated Z level probe signal information such that it is continuously available for periodically refreshing video display 38 in conjunction with converter 108, and for retrieval via microprocessor 100 and terminal 48 for printout on a hard copy or other permanent recording medium such as magnetic tape or disk.

Summarizing the features and capabilities of system 11 as thus far described, it will be appreciated that sophisticated, nondestructive testing method and apparatus are provided for effectively testing such state-of-the-art airfoil structures as adhesive bonded and advanced fiber reinforced resin composite materials. Testing of such airfoil structures is facilitated by the portability of system 11, and capability of forming a permanent inspection record of the structure. The video display lends itself to rapid and accurate diagnosing of fault or other structural aberrations. The recording or storing of the inspection data is initially in the form of binary signal information stored in an erasable and updatable memory, namely in memory and timing circuit 106, and the display of such stored data is effected on video display 38 as described above in connection with FIGS. 6 and 7.

A system 11 implementd in accordance with this disclosure has proved capable of achieving an X,Y resolution of 0.01 inches with a ±0.01 repeatability and a measurement repeat rate of 0.4 seconds between successive X,Y positions, for an area 14 spanning 2 by 2 feet. To achieve the resolution and measurement repeat rate mentioned, system 11 incorporates certain additional features, described in the following section of disclosure, including averaging clockwise and counter-clockwise determined values for the angles $\alpha_p$ and $\beta_p$ and enabling a selection between a large angle scan mode in which sensors 20a and 20b sweep through a full quarter arc at the respective corners of area 14, and a small angle scan mode (dither) in which each of sensors 20a and 20b oscillate in a relatively smaller arc such as ±15° relative to the position of module 16. The small scan mode enables a more rapid response to probe module movement by position determining control 40.

Operation of Controls 40 and 42

As mentioned above, each of controls 40 and 42 incorporate a separate, programmed microprocessor that functions to respectively carry out the tasks of controlling sensors/scanner assembly 18, correlating the probe output signal with probe position coordinates and formatting the resulting signals for presentation on video display 38. For this purpose, microprocessor 100 of control 42 is responsive to commands entered at terminal 48 (FIG. 6) to supervise the operations of both controls 40 and 42 as more fully described below in connection with the flow charts and commands shown in FIGS. 8–11. Concurrently, control 40 operates in response to its own internal microprocessor 80 (FIG. 6) to control sensors/scanner assembly 18 so as to develop position coordinate signals that are made available by microprocessor 80 for communication to control 42 for correlation with the NDT Z level signal developed by the probe 50 of module 16. The operations performed by microprocessor 80 of control 40 are depicted in the flow diagrams and routine lists of FIGS. 12–26.

As mentioned above, any one of a number of commercially available microprocessors may be employed for the microcomputations in controls 40 and 42, programmed in accordance with a desired processor language to carry out the specific disclosed functions. By way of illustration, using the particular microprocessors and associated support components as described herein above, controls 40 and 42 are programmed in accordance with PLM langauge to operate in accordance with the functions, sequences and processing steps described below in connection with FIGS. 8–26. Alternatively, these operations of controls 40 and 42 may be implemented by specific, dedicated logic and control circuitry as will be recognized by those skilled in this field.

Figure 8:
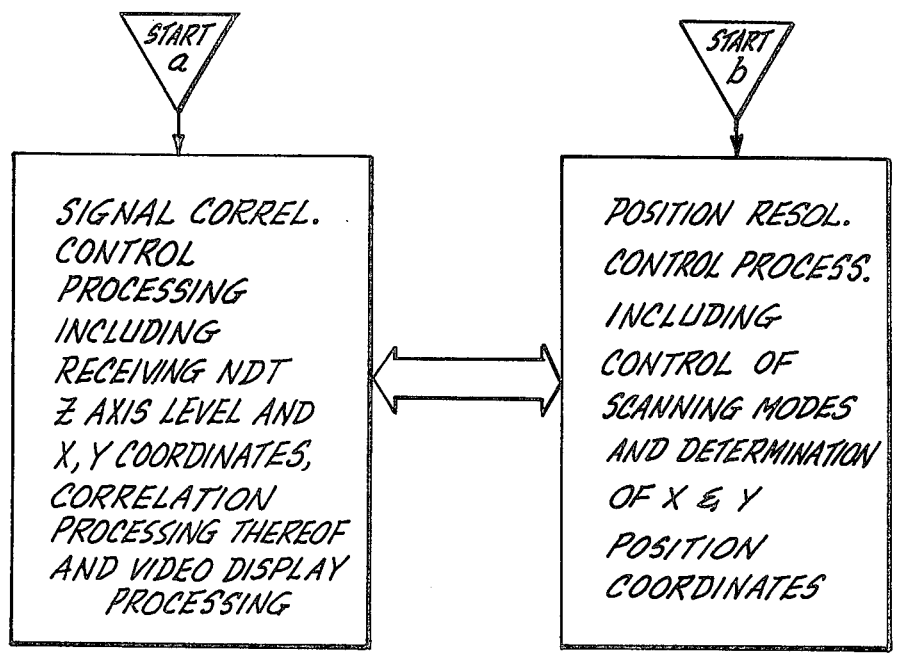

Thus with reference to FIG. 8, an overview of the signal processing performed by controls 40 and 42 is depicted in which the microprocessor of control 42 is independently initiated at START a by means of entries made at terminal 48 (FIG. 3) to perform the tasks of receiving the NDT Z axis level from probe/light source module 16, and the X,Y position coordinates from control 40, of correlating these signals and performing the video display processing needed to properly format the correlated signals for presentation on video display 38 (FIG. 3). The position resolving signal processing performed by control 40 is started independently at START b as shown in FIG. 8, but once initiated, this processing is carried out under the supervision of signal correlation 42 control which in turn is responsive to operator commands entered at terminal 48 (FIG. 3). The position resolving control processing includes control of the scanning modes of sensors/scanner assembly 18, and determination of the X,Y position coordinates. Signals representing such determined coordinates are fed to the signal correlation control 42 for processing pursuant to a handshake operation between controls 40 and 42 as described more fully below.

Figure 9:
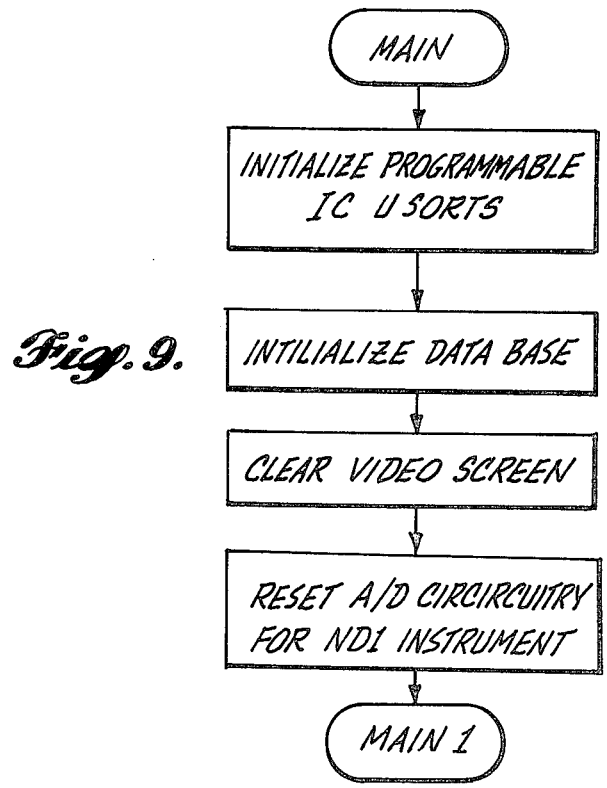

The signal correlation control processing shown generally in FIG. 8 is depicted in more detail in FIGS. 9–11. A first routine entitled MAIN is shown in FIG. 9 and provides for certain initialization procedures to set up the data base, place the IC USARTS in the proper initial mode, clear the video display and reset the NDT instrumentation.

Figure 10A:
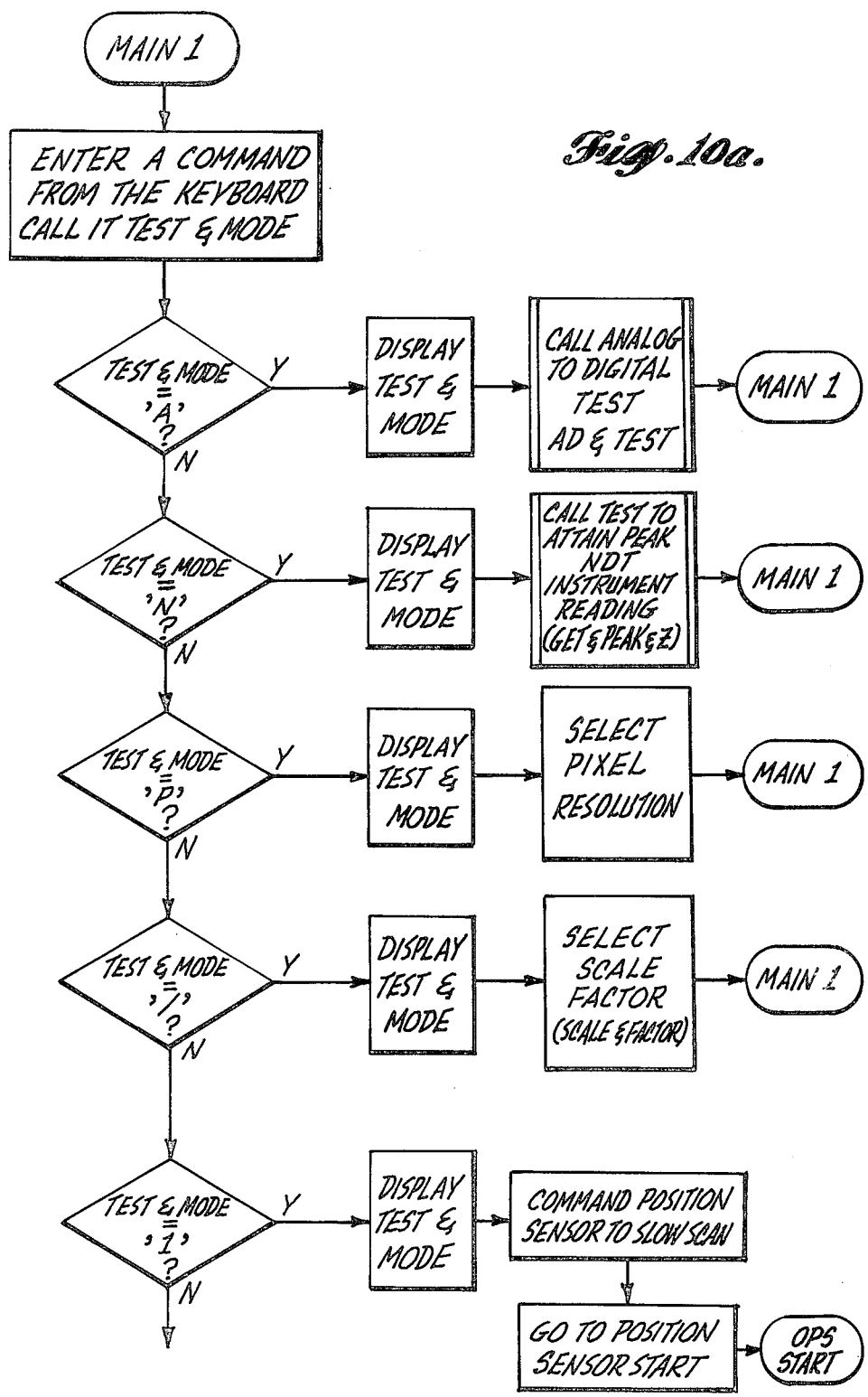
Figure 10B:
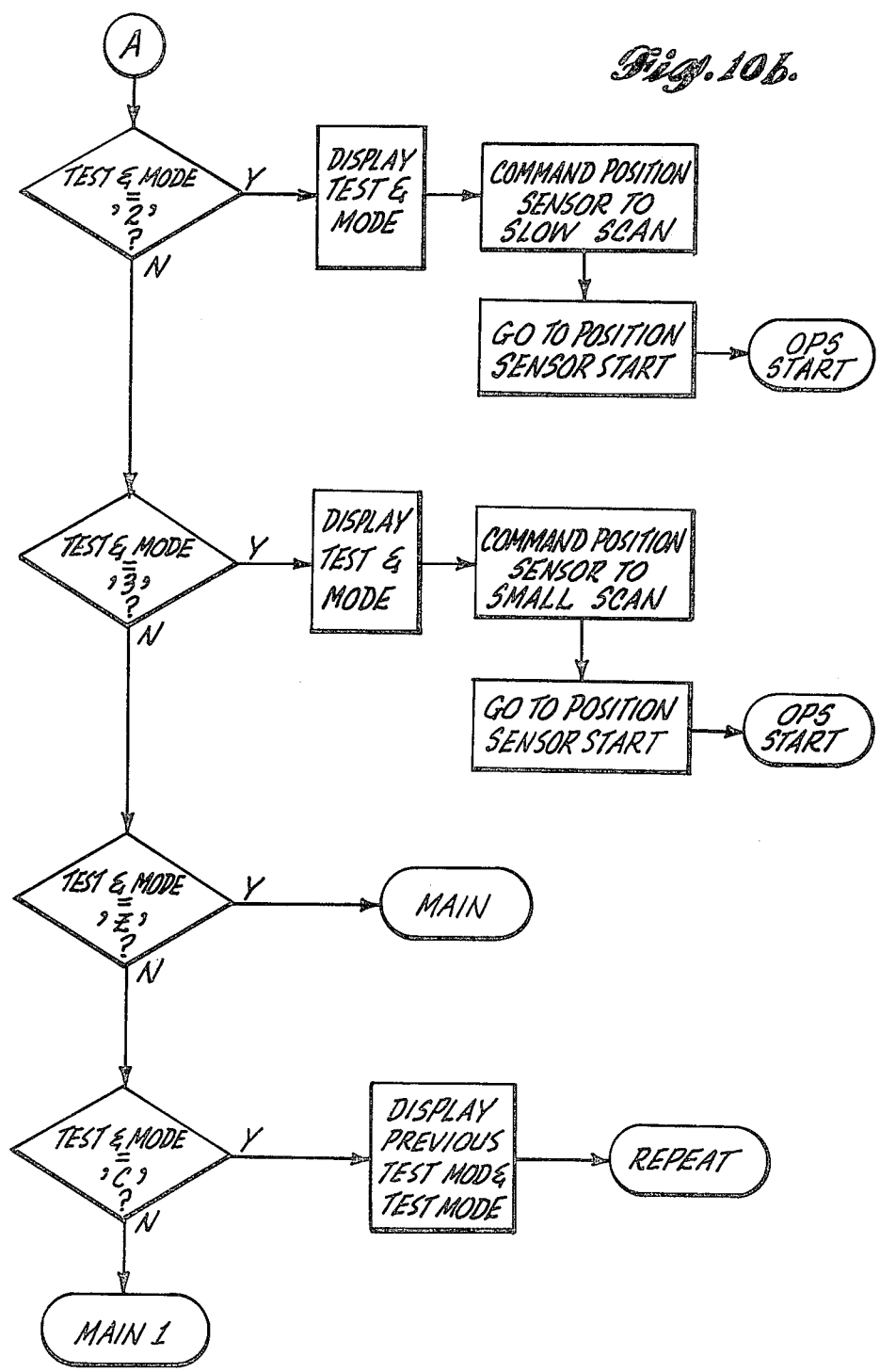

Following these initialization steps, control 42 advances to a routine entitled MAIN 1 which is shown in FIGS. 10a and 10b and which interrogates terminal 48 (FIG. 3) for various possible command modes entered by an operator including such selectable modes as resolution, scale, type of scan performed by sensors/scanner assembly 18, etc. In particular, the routine of MAIN 1 proceeds through a sequence of cascaded decision blocks, each of which determines whether a particular input command has been entered on the keyboard and if so diverts the flow of the processor to an appropriate subroutine also indicated in FIGS. 10a and 10b. A list of the commands decoded by MAIN 1 is set forth in FIGS. 10c and 10d, wherein the function of each command is described. These command functions can be generally classified as follows: commands PXX, /XX, and Z set up the graphics on the video display; N controls the receipt and digitizing of the NDT probe level; commands 1, 2, and 3 select the desired scan mode, respectively, SLOW, FAST, or SMALL, the characteristics of each of which are described more fully hereinafter; and command A is used for testing and debugging the system by displaying a digitally encoded value of the analog NDT probe level.

If any one of the available scanning modes 1, 2 or 3 are selected and entered on the keyboard, MAIN 1 will decode such mode selection and direct the processing flow to a routine entitled OPTICAL POSITION SENSOR (OPS) and in conjunction therewith command the OPS routine to assume either the SLOW SCAN in response to test mode 1, a FAST SCAN in response to test mode 2 and a SMALL SCAN in response to test mode 3, as indicated in FIGS. 10a and 10b. Thus in the MAIN 1 routine, control 42 will decode each of the commands, A, N, PXX and /XX and then loop back to the beginning of MAIN 1 as indicated in FIG. 10a, and will decode each of the test mode commands 1, 2 or 3 and direct the control 42 to OPS START for performing the optical position sensor routine shown in FIGS. 11a, b and c. The remaining commands of Z and C respectively cause control 42 to return to MAIN for reinitialization of the video display, and to repeat a previously commanded test mode.

Figure 11A:
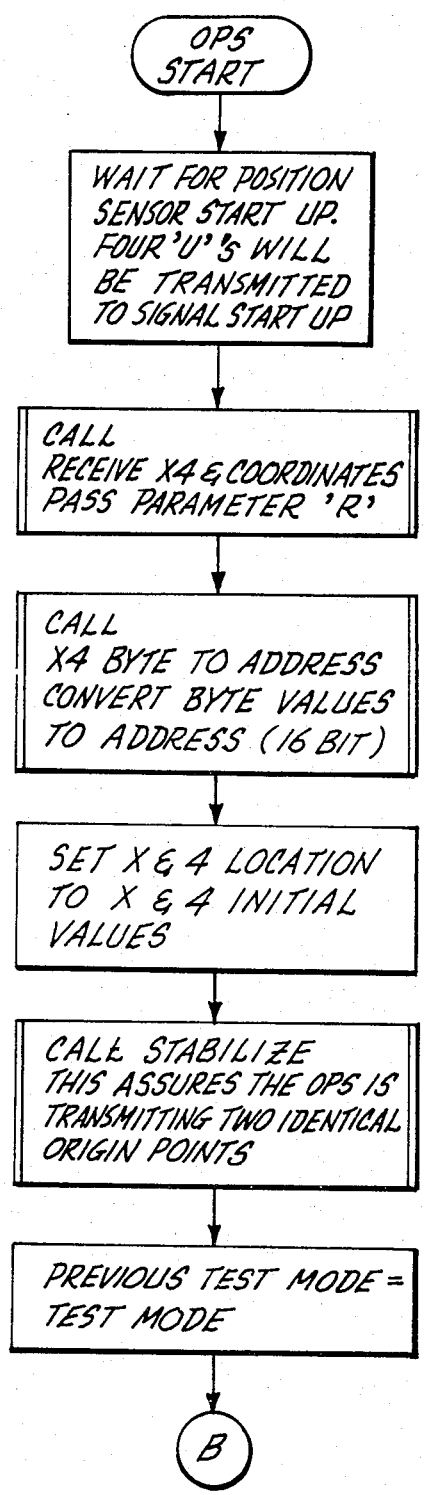

The OPS routine shown in FIGS. 11a, b and c performs initialization of signal correlation control 42 for receiving the X,Y position coordinates from position resolving control 40 and for this purpose OPS performs a handshaking operation with the microprocessor of control 40 in which control 40 transmits via I/O port 94 (FIG. 6) a sequence of four U's in ASCII code which is decoded by OPS in control 42 to establish the handshake and prepare control 42 for receiving the X,Y position coordinates. Upon receipt of such coordinates, OPS sends a code pass parameter R again in ASCII code back to the microprocessor of control 40 to acknowledge the receipt of the coordinates. Following these operations, OPS converts the X,Y coordinates to a byte address compatible with the mapped memory of circuit 106 (FIG. 6) formatted for outputting the position coordinates in a suitable sequence for being displayed by video display 38. Next OPS sets the X and Y locations to initial values corresponding to X=0 and Y=0 establishing the origin of the X and Y field 14 (FIG. 2). Thereafter a routine called STABILIZE is called and this subroutine provides for detection of a stable position of the hand held sensor/light source module 16 (FIG. 2) so that data is not read into controls 40 and 42 while the operator is still moving module 16. Following the STABILIZE subroutine, OPS the previous test mode to the current test mode in order to cooperate with the REPEAT output of MAIN 1 to allow the system to continue processing data from previously initialized conditions without requiring reinitialization through MAIN 1.

Figure 11B:
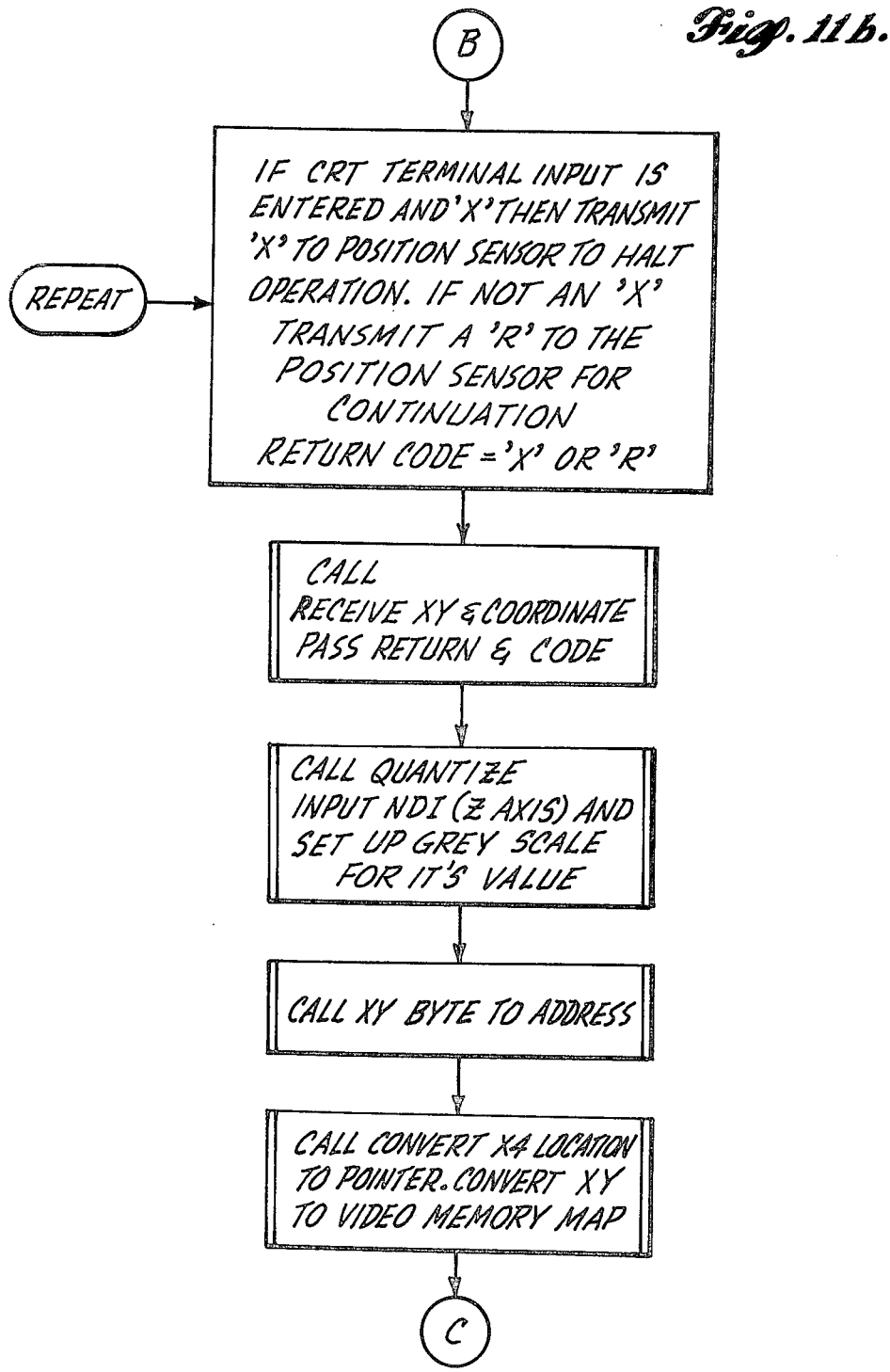

The continuing sequence of routines shown in FIG. 11b involve an operation for decoding a stop or halt command X which can be entered by the operator at the keyboard of terminal 48 to cause the processing in OPS to be halted. Thus, if an X has been entered at the keyboard terminal, OPS will stop its processing operations and will not send an R code to position resolving control 40. Thus, the X code terminates the handshake between control 42 and control 40. Conversely, if OPS is to continue processing the position coordinates, the R code is returned to control 40 and OPS proceeds with a routine for receiving the X,Y coordinate positions as indicated by the succeeding subroutine in the sequence shown in FIG. 11b. Thereafter, OPS calls a routine entitled QUANTIZE by which the output Z level from the NDT probe 50 of module 16 (FIG. 6) is quantized and stored along with the X,Y position coordinates in memory 106 (FIG. 6). The quantization of the Z level is accomplished as briefly described above by providing in memory 106 a plurality of binary encoded banks of X,Y position memory and storing in appropriate such banks the X and Y position bytes as needed to form, in binary, the established quantized value of the Z axis level of the NDT probe signal. This operation establishes the above-mentioned grey scale for subsequently displaying on video display 38 the quantized magnitude of the NDT probe signal as a varying grey video level and as a function of probe position. The final subroutine of OPS is shown in FIG. 11b to provide for converting by means of converter 108 the X and Y locations and correlated and quantized Z level data held in memory 106 into a video memory-mapped format suitable for driving a CRT in a conventional manner to produce the video display.

Figure 11C:
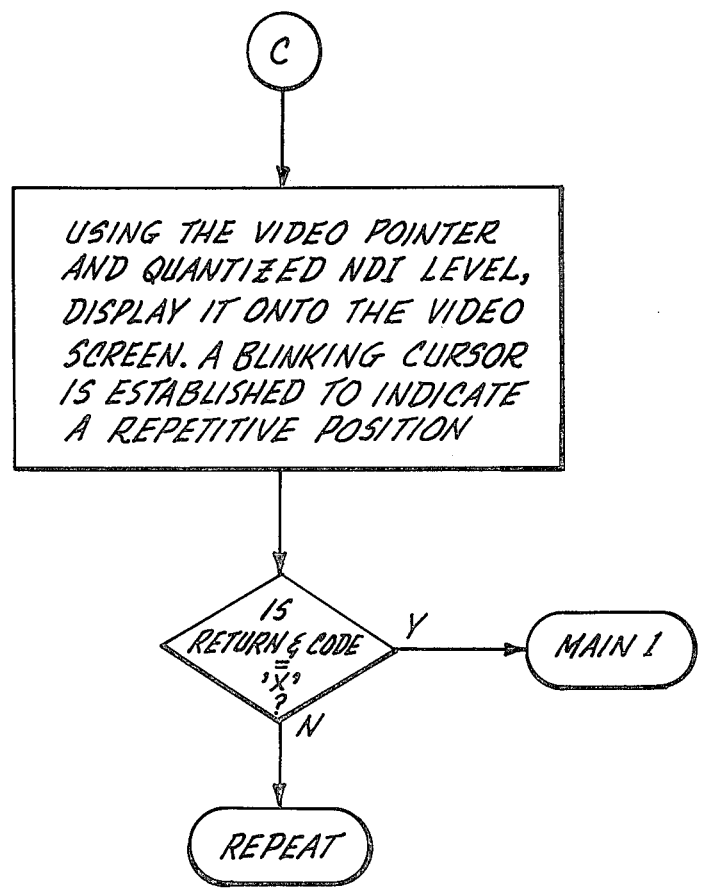

In FIG. 11c, the OPS routine is shown to include an operation for effecting the display of the quantized NDT Z level on to the screen of the CRT of display 38 and for producing a blinking cursor at the present location of module 16, namely the location where the most recent position coordinates and Z level signals are generated.

So long as an X code is not received by OPS, the decision block in FIG. 11c will cause the OPS routine to continue looping back to the REPEAT pointer shown in FIG. 11b so as to continue processing the X, Y and Z data in accordance with the subroutines shown in FIGS. 11b and 11c. If an X code is entered on terminal 48, then the decision block in FIG. 11c of the OPS routine will return the flow of the program to MAIN 1 for decoding the various possible input commands referred to in connection with FIGS. 10a, b, c and d above.

Figure 12:
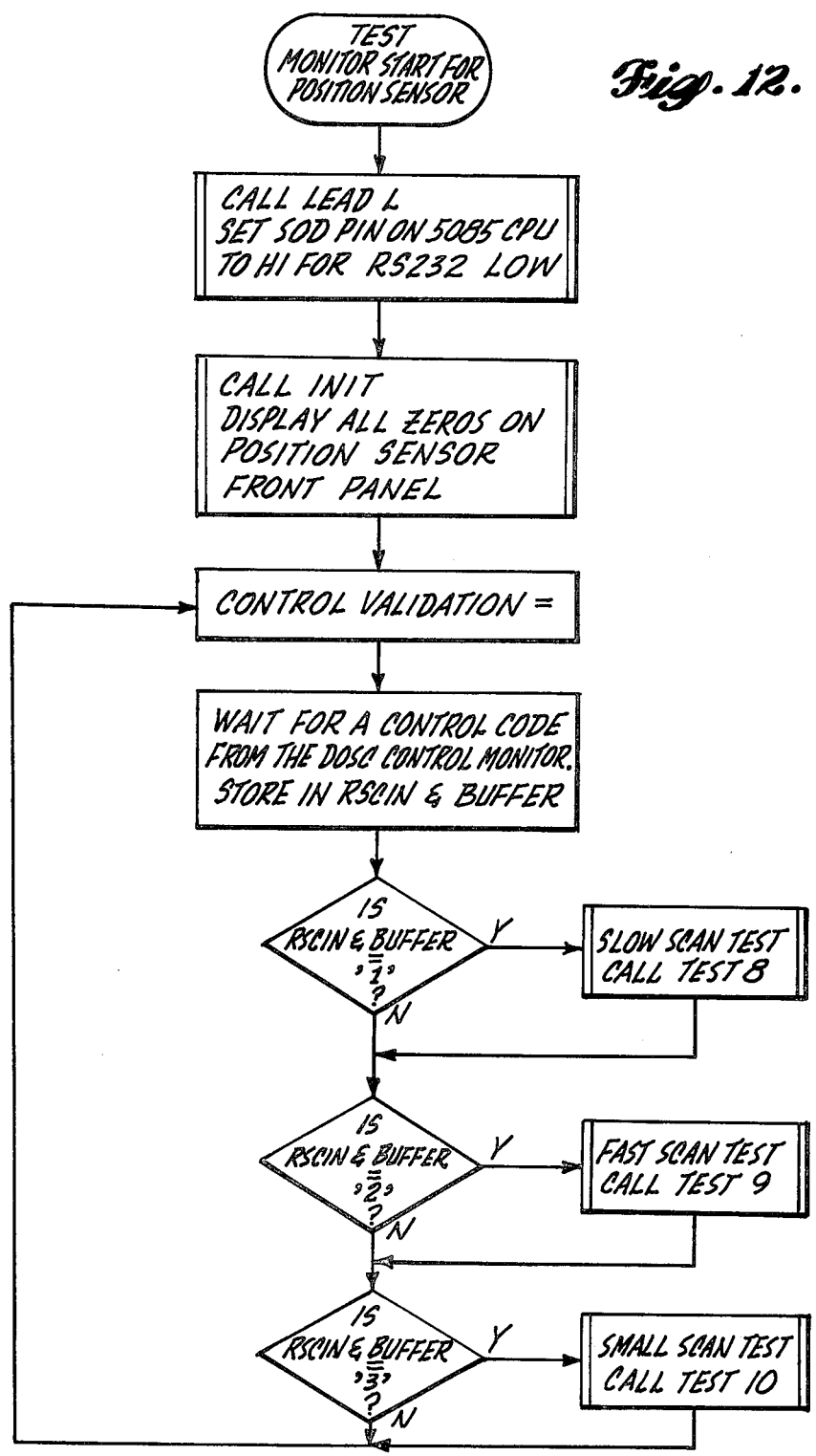

The remaining flow diagrams of FIGS. 12-26 pertain to the operations of the sensors/scanner assembly 18 governed by position-resolving control 40. Of these flow diagrams, FIG. 12 shows a test monitor procedure called TSTMON by which the above-mentioned handshake between control 40 and control 42 is established for the transmission of the position coordinates from the former to the latter. TSTMON is powered up and initialized on its own irrespective of the operating status of control 42. The CONTROL VALIDATION label refers to the operation block in which the TSTMON routine looks for a command code from control 42 before going forward with the execution of the TSTMON routine. The label RSCIN and associated buffer refers to a memory location for storing the control code in the memory associated with the microprocessor of control 40. Thereafter, TSTMON decodes the selected one of three possible scanning modes, SLOW SCAN (test 8), FAST SCAN (test 9), and SMALL SCAN (test 10) are decoded and the appropriate test routine called up for execution.

Figure 13:
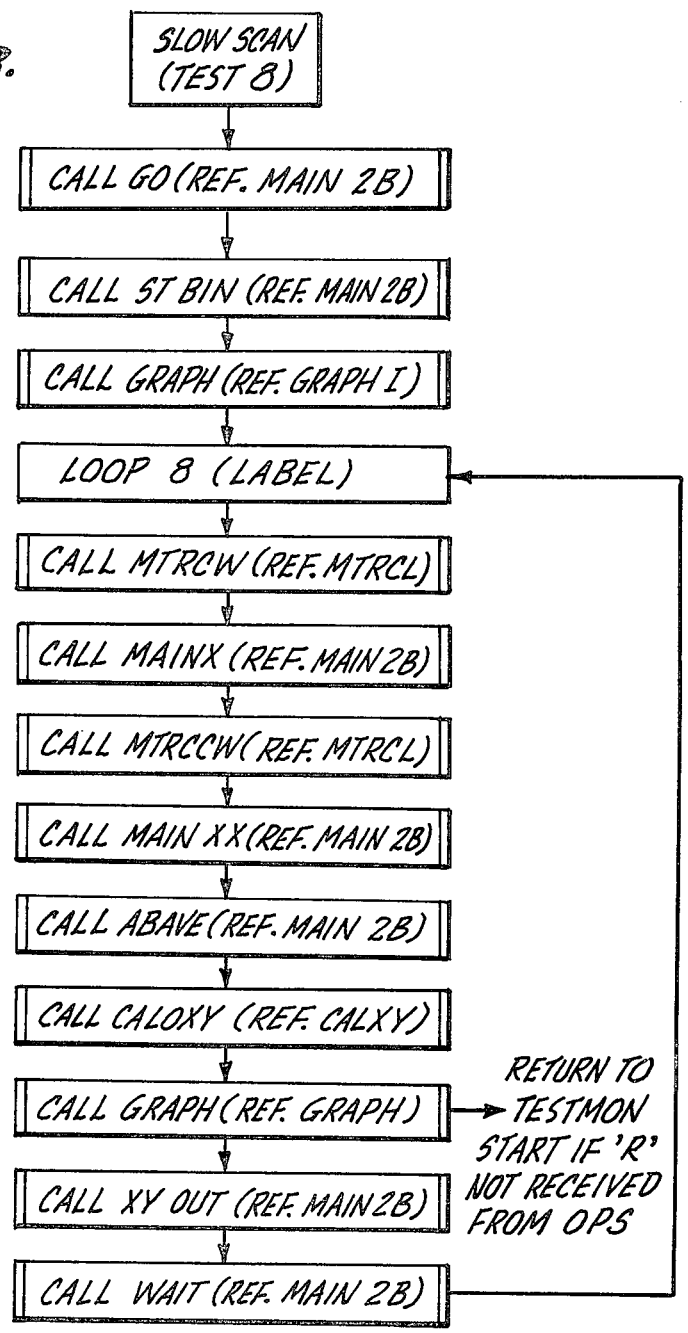

A flow diagram entitled SLOW SCAN (test 8) is shown in FIG. 13 to include a series of successively executed subroutines, the performance of which in general provides for cycling each of sensors 20a and 20b through a large scan angle of 110° selected to be slightly greater than the 90° right angle at each corner of the rectangular testing field 14 (see FIG. 2), and to produce X,Y position coordinates from this scanning operation and pass the X,Y position data on to control 42 for further processing thereby.

For this purpose, the SLOW SCAN (test 8) of FIG. 13 includes a series of initialization routines entitled GO, STBIN, and GRAPH I, the functions of which are described in the lising of general subroutines shown in FIG. 15a. After such initialization, the SLOW SCAN routine enters a repeating loop commencing with the label LOOP 8 which incorporates the successive operations of MTRCW, MAINX, MTRCCW, MAINXX, ABAVE, CALCXY, GRAPH, XYOUT and WAIT. These operations are described in FIGS. 15a, b and c in which MRTCW and MTRCCW provide for movement of the sensor scanning motors for a predetermined number of steps to encompass the desired scanning angle of 110°, MAINX and MAINXX provide for reading out the alpha and beta angle counts from the associated encoders and angle counters described above in connection with assembly 18. ABAVE is a routine that averages the alpha and beta angles for both clockwise and counter-clockwise directions of each sensor movement across the position of the probe/light source module 16 and CALCXY determines the X,Y position coordinates from the measured angles alpha and beta and the distance d separating the sensors using a triangulation formula. GRAPH is a routine that transmits the X,Y position coordinates into a video processing section of control 42 provided by memory and timing circuit 106 shown in FIG. 6. XYOUT processes the X,Y position coordinates for presentation on display 92 (FIG. 6) and WAIT is a fixed delay that introduces a pause between each scanning cycle of sensors/scanner assembly 18 for slowing down the scanning operation as the SLOW SCAN routine executes the processing loop commencing with label LOOP 8.

In FIG. 14, a FAST SCAN (test 9) routine is shown for controlling the sensors/scanner assembly 18 in a relatively faster scanning operation. The routine for this mode is essentially the same as the SLOW SCAN (test 8) mode except that the interposed delay provided by the WAIT routine is omitted in the FAST SCAN routine of FIG. 14 so that the sensors 20a and 20b sweep back and forth through their scanning angles without pausing between scans. Otherwise the processing is the same as described in connection with FIG. 13 resulting in the calculation of X,Y position coordinates, transferring such data to the video display processing section of control 42 and causing the X,Y coordinates to be presented on display 92 (FIG. 6).

As briefly mentioned above, FIGS. 15a, b, and c set forth the descriptions of each of the general purpose subroutines used in the SLOW SCAN (test 8) and FAST SCAN (test 9) as described above and in a third selectable mode, described hereinafter and entitled SMALL SCAN (test 10). Of the general subroutines listed in FIGS. 15a and 15b the averaging subroutine ABAVE is shown in greater detail in the flow diagram of FIGS. 16a and 16b, and the calculation subroutine of CALCXY is shown in greater detail in the flow diagram of FIG. 7.

Figure 16A:
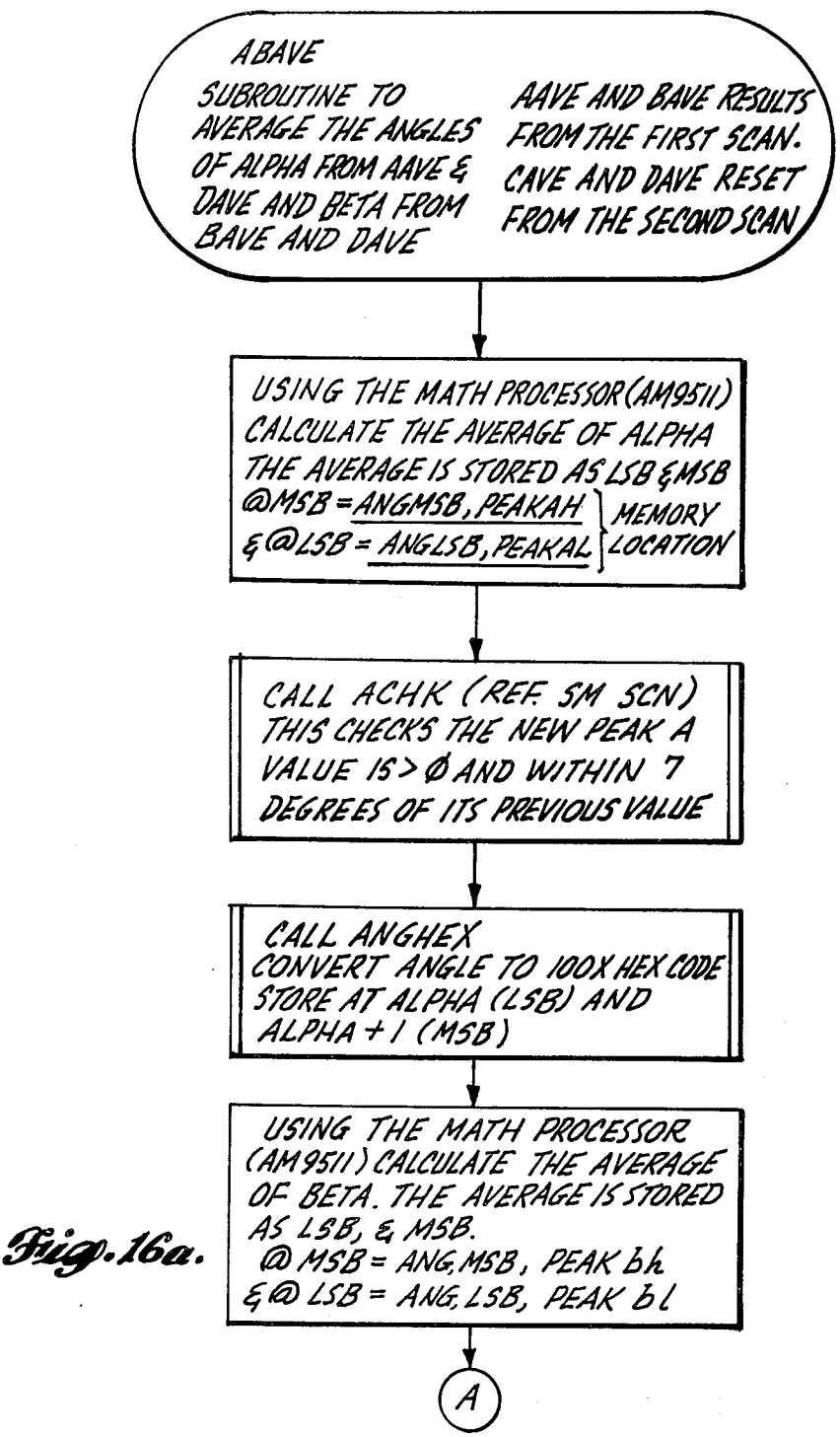
Figure 16B:
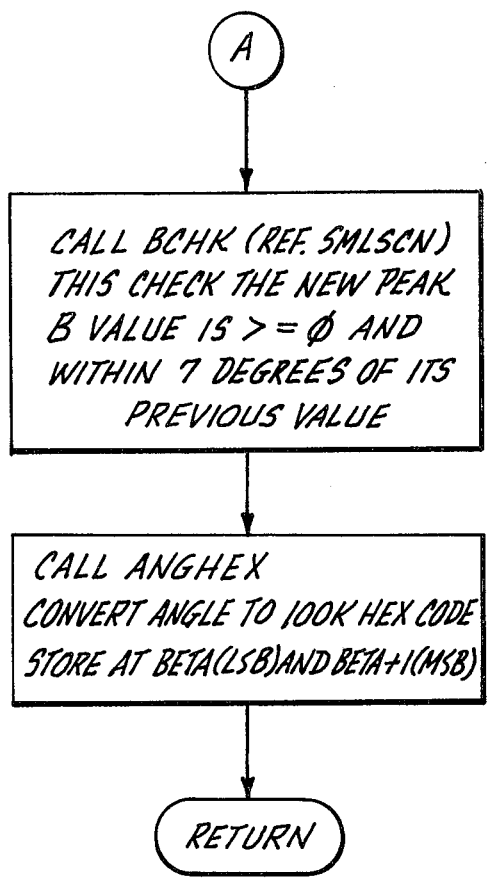

With reference to FIGS. 16a and 16b, ABAVE provides for averaging the angles of alpha from angle data stored at AAVE and CAVE resulting respectively from the first and second half cycles of the scanning arc of sensor 20a for angle alpha; and for averaging the angles of beta from BAVE and DAVE which store the beta angle data for the first and second half cycles of scanning arcs of the sensor 20b. A first operation of this routine averages the alpha angle data in math processor 84 (FIG. 6) and store the results in groups of 8 bit bytes as the least significant bits (LSB) and most significant bits (MSB) and stores the most significant bit results at memory locations identified by Angmsb peak ah and the least least significant bit data at Anglsb, peak al. A succeeding operation called ACHK, used in the SMALL SCAN processing described below in connection with FIGS. 19-26 determines whether the new alpha data peak A value is greater than zero and within 7° of its previous value for the purpose of carrying out the SMALL SCAN operation. Thereafter a routine entitled ANGHEX converts the alpha data to 100 times hex code and stores the results at the memory locations alpha and alpha +1 for the least significant and most significant bits respectively. The foregoing operations are repeated for the beta angle and upon completion thereof the flow of the operations returns to the processing routine of tests 8, 9 or 10.

Figure 17:
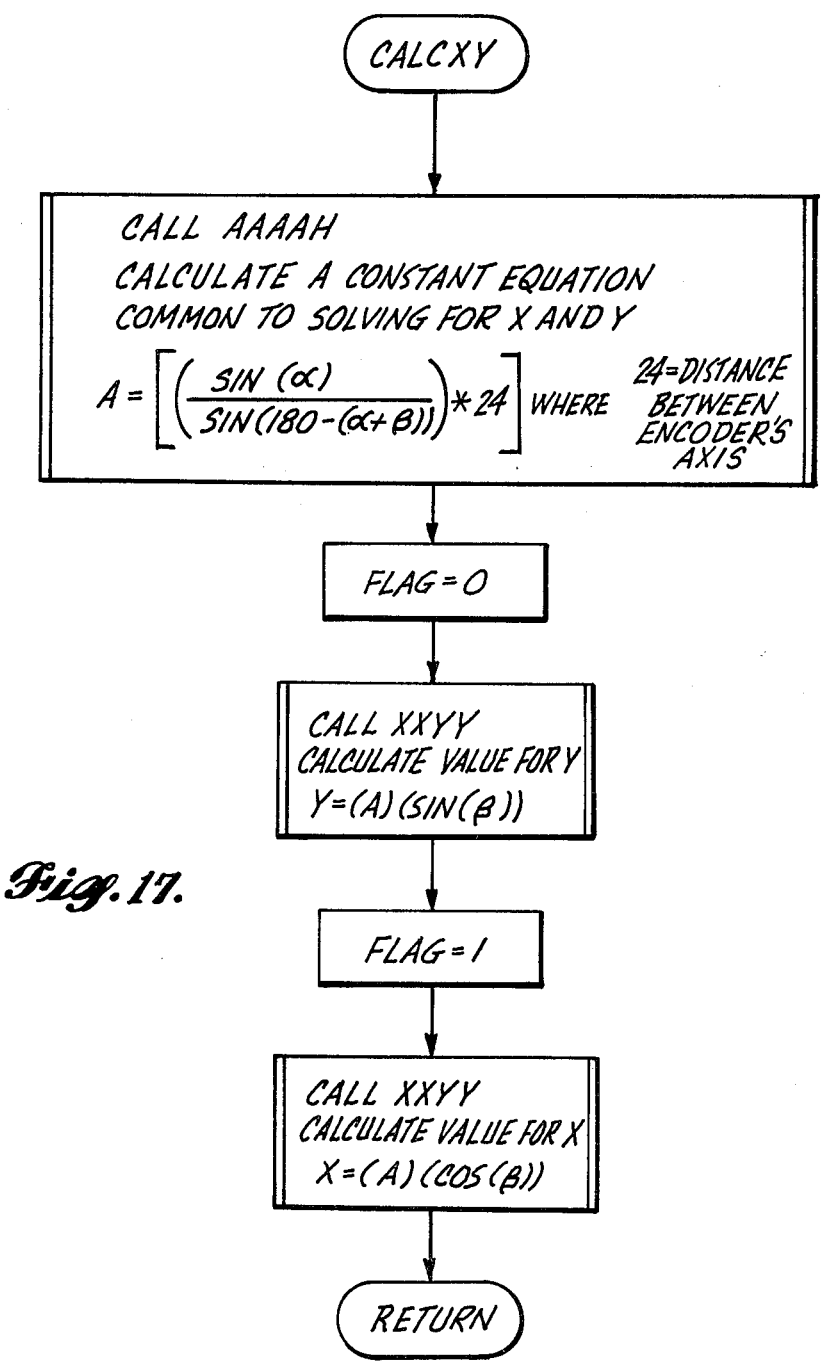

With reference to FIG. 17, the CALCXY performs the necessary triangulation processing of the angle data for alpha and beta and of the given distance d between the sensors 20a and 20b to produce digitally encoded signals representing the X,Y position coordinates.

Figure 18A:
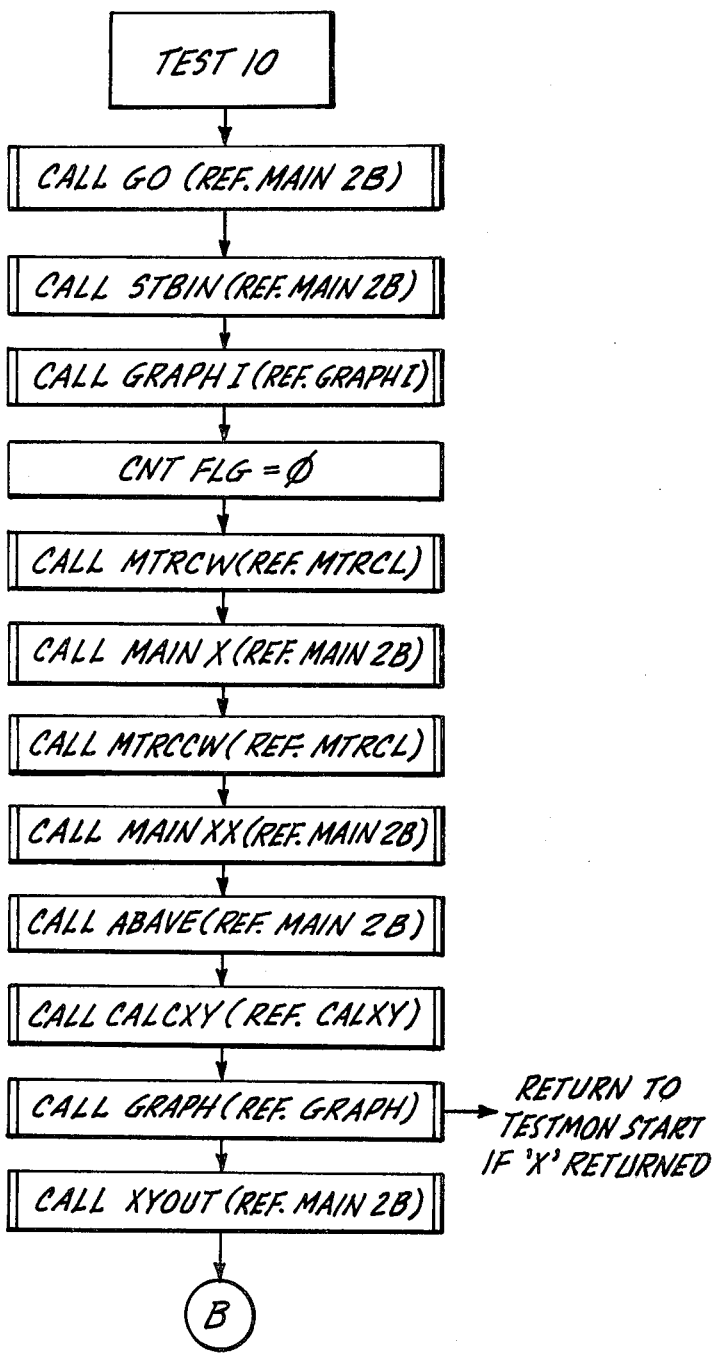
Figure 18B:
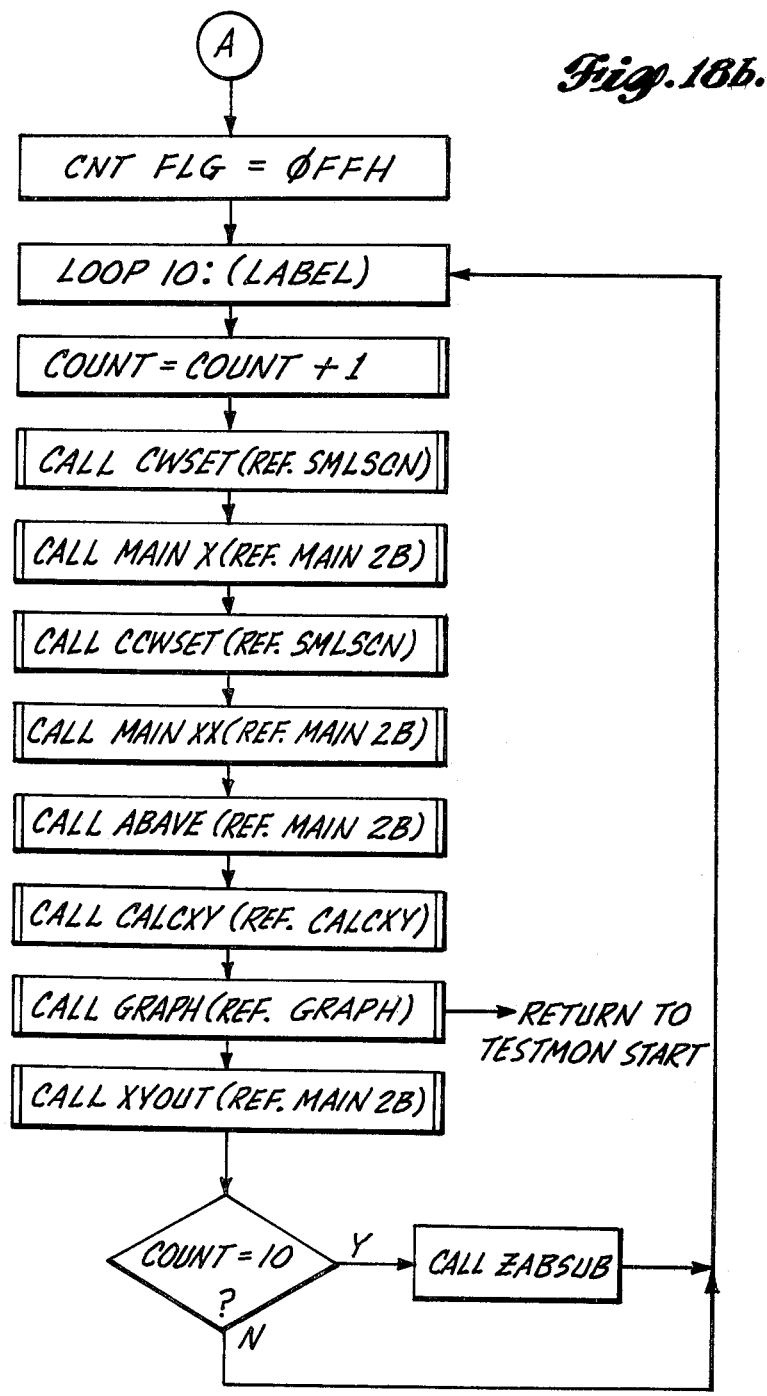

The SMALL SCAN (test 10) mode shown in the flow chart of FIGS. 18a and 18b causes the sensors 20a and 20b to dither in a relatively small scanning arc about the last determined position of the module 16. For this purpose, the SMALL SCAN routine includes a first phase in which the sensors are caused to scan through the large angle arc similar to the FAST SCAN mode described above in connection with FIG. 14 to locate the present position of module 16, and a second phase in which the SMALL SCAN mode produces a dither operation of the sensors through an arc of approximately 30°, being ±15° of the last determined position of module 16. During each dither cycle, an updated position of module 16 is determined and that updated position is then used as the center point for the succeeding dither cycle.

Thus, with reference to FIG. 18a, the first phase of the SMALL SCAN routine is shown to include the same series of operation described above in the FAST SCAN mode of FIG. 14 with the addition of a phase control operation whereby the label CNT. FLG. is set to 0. Thereafter, during the second phase or dither mode of the SMALL SCAN routine the CNT. FLG. will be set to a different value 0FFH as indicated in FIG. 18b to instruct the program to thereafter to perform the small angle dither rather than repeating the large angle initial scan shown in the diagram of FIG. 18a.

Thus, with reference to FIG. 18b, the dither phase of the SMALL SCAN mode is initiated by changing CNT. FLG. as indicated then entering a dither loop labeled LOOP 10 which includes the series of operation of COUNT, CWSET, MAINX, CCWSET, MAINXX, ABAVE, CALCXY, GRAPH and XYOUT. At the end of this series of operations, a decision block determines whether the count equals 10 and if so a subroutine called ZABSUB is called for a transition to the alpha and beta angles zeroing routine of ZAB.

The COUNT OPERATION in loop 10 provides for counting up to ten cycles of the SMALL SCAN dither and then at the end of ten full cycles, rezeroing the alpha and beta sensors 20a and 20b in accordance with the ZAB subroutine described more fully below in connection with FIGS. 26a and 26b.

The above mentioned operations performed in the second or dither phase of the SMALL SCAN mode are described in the listing of the special subroutines in FIGS. 19a, 19b, and 19c. Of these, the COUNT FLG. and COUNT OPERATIONS are described above. The CWSET causes the alpha and beta sensors 20a and 20b to be moved according to a number or Count steps developed in a routine entitled CWCNT which operates to determine the number of clockwise and counter-clockwise steps required for the alpha and beta sensors to move each sensor in a first dither half-cycle past the last location (referred to as last peak angle) of module 16 plus a fixed overshoot angle of 15°. The Counts for stepping the motors that move the alpha and beta sensors 20a and 20b are produced by developing a value I equalling the required clockwise steps for the alpha sensor 20a and a value J equal to the required counterclockwise steps for the beta sensor 20b in which the I and J values are used in further subroutines ACWAB and ACCWAB as more fully described below.

Figure 24:
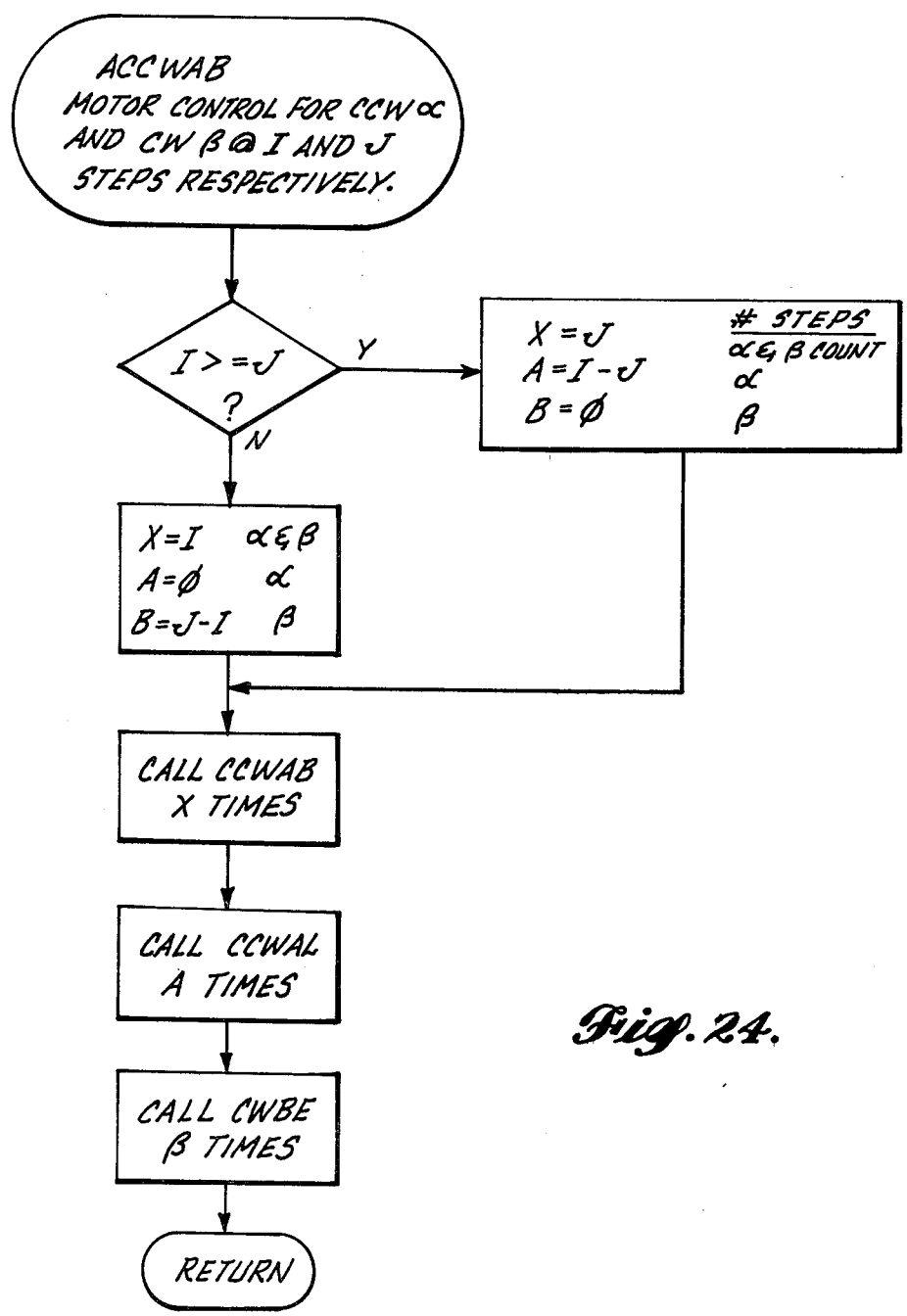

A subroutine entitled CCWSET is the counterpart of CWSET and provides for moving sensors 20a and 20b in the opposite direction by approximately 30° to complete the last half cycle of the SMALL SCAN dither, and this subroutine is implemented by calling up ACCWAB. The flow diagram of CWSET is set forth in FIG. 20; CCWSET in FIG. 21; CWCNT in FIG. 22; ACWAB in FIG. 23, and ACCWAB in FIG. 24. It is observed that the ACWAB diagram of FIG. 23 and the related flow diagram of ACCWAB of FIG. 24 provide for moving the alpha and beta sensors 20a and 20b in concert through the number of common steps which each must be moved for a particular dither cycle, and for moving the sensors separately for the balance of the required dither cycle steps. In this regard it is noted that unless the module 16 is located precisely on a perpendicular bisector between the two sensors 20a and 20b, the dither angles for each sensor will be different and hence the required difference in control steps required of the ACWAB and ACCWAB subroutines of FIGS. 23 and 24.

Figure 25:
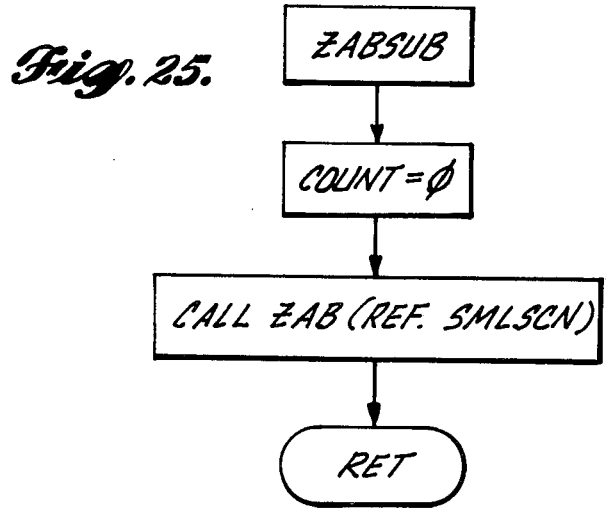
Figure 20:
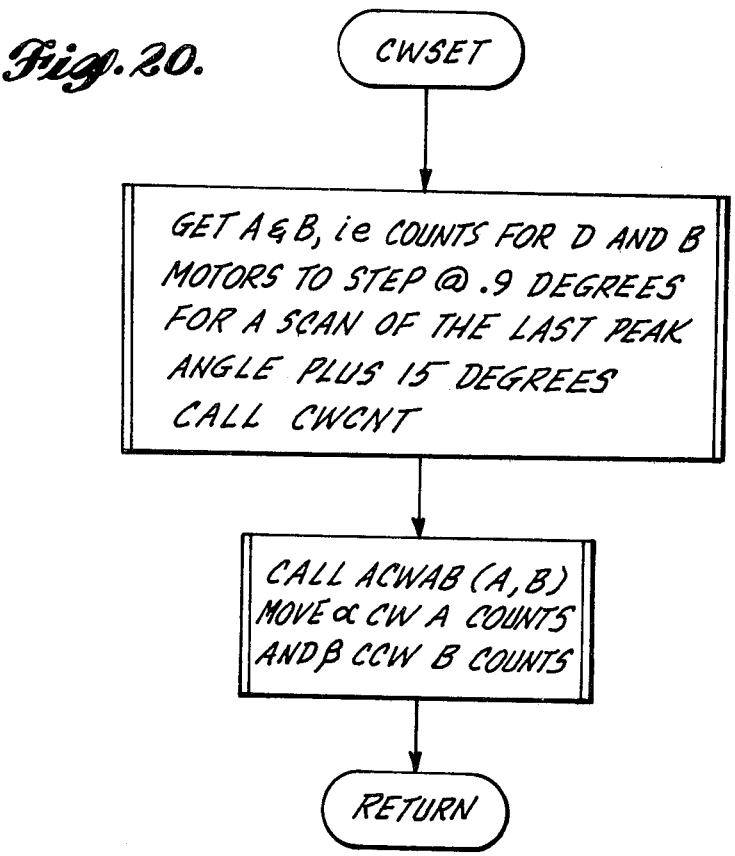
Figure 21:
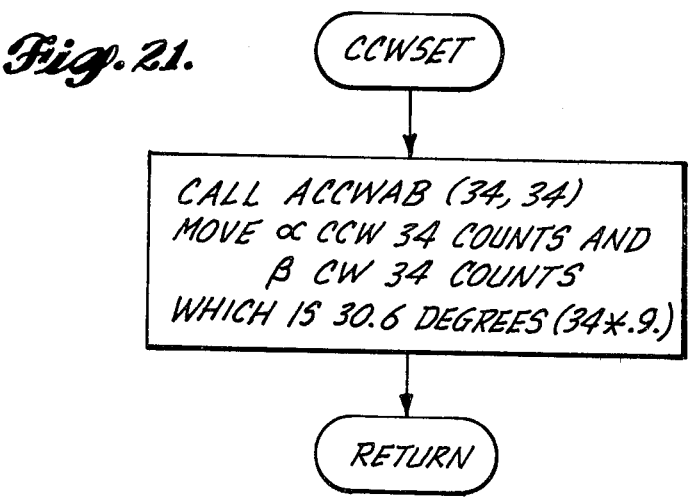
Figure 22:
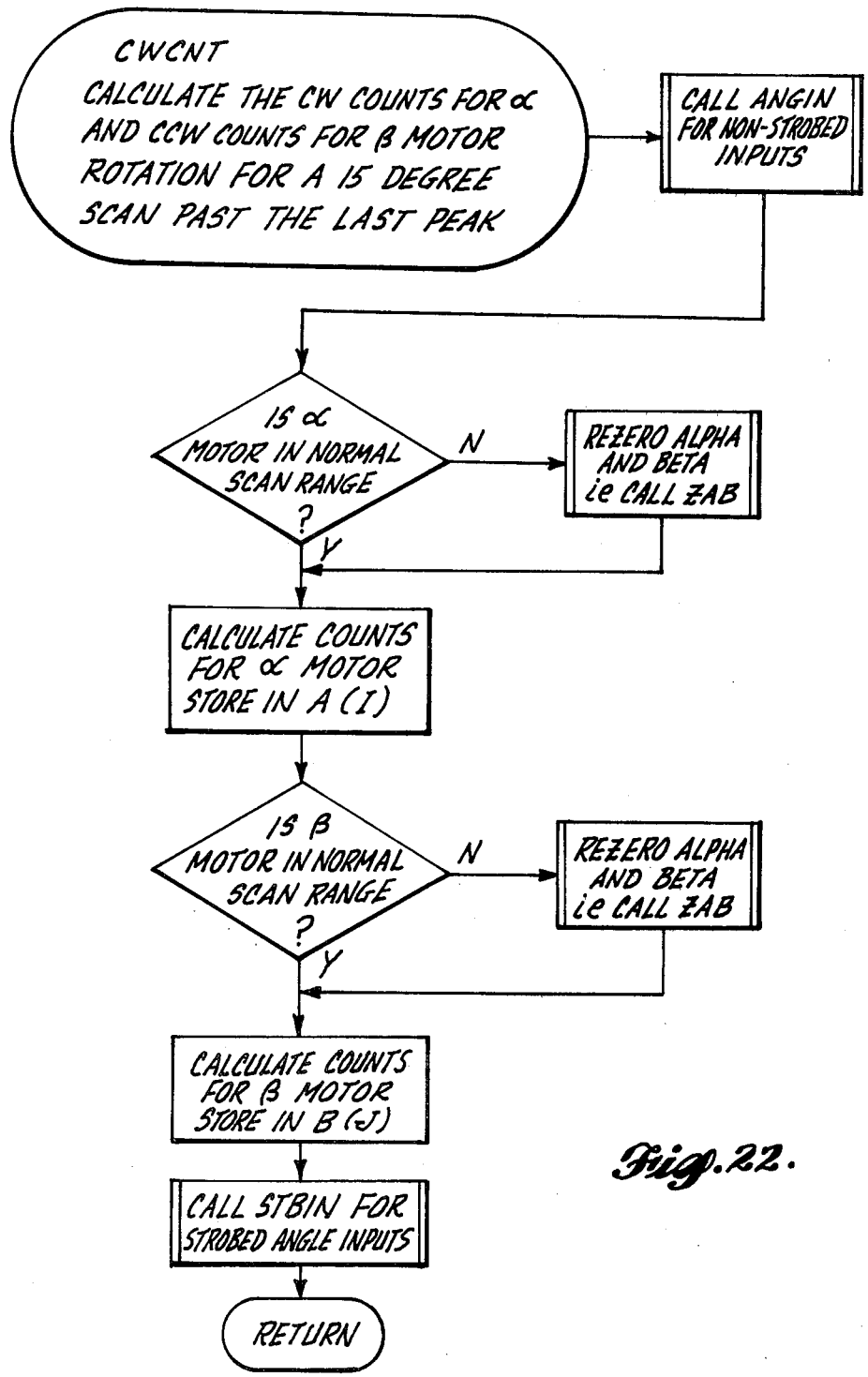
Figure 23:
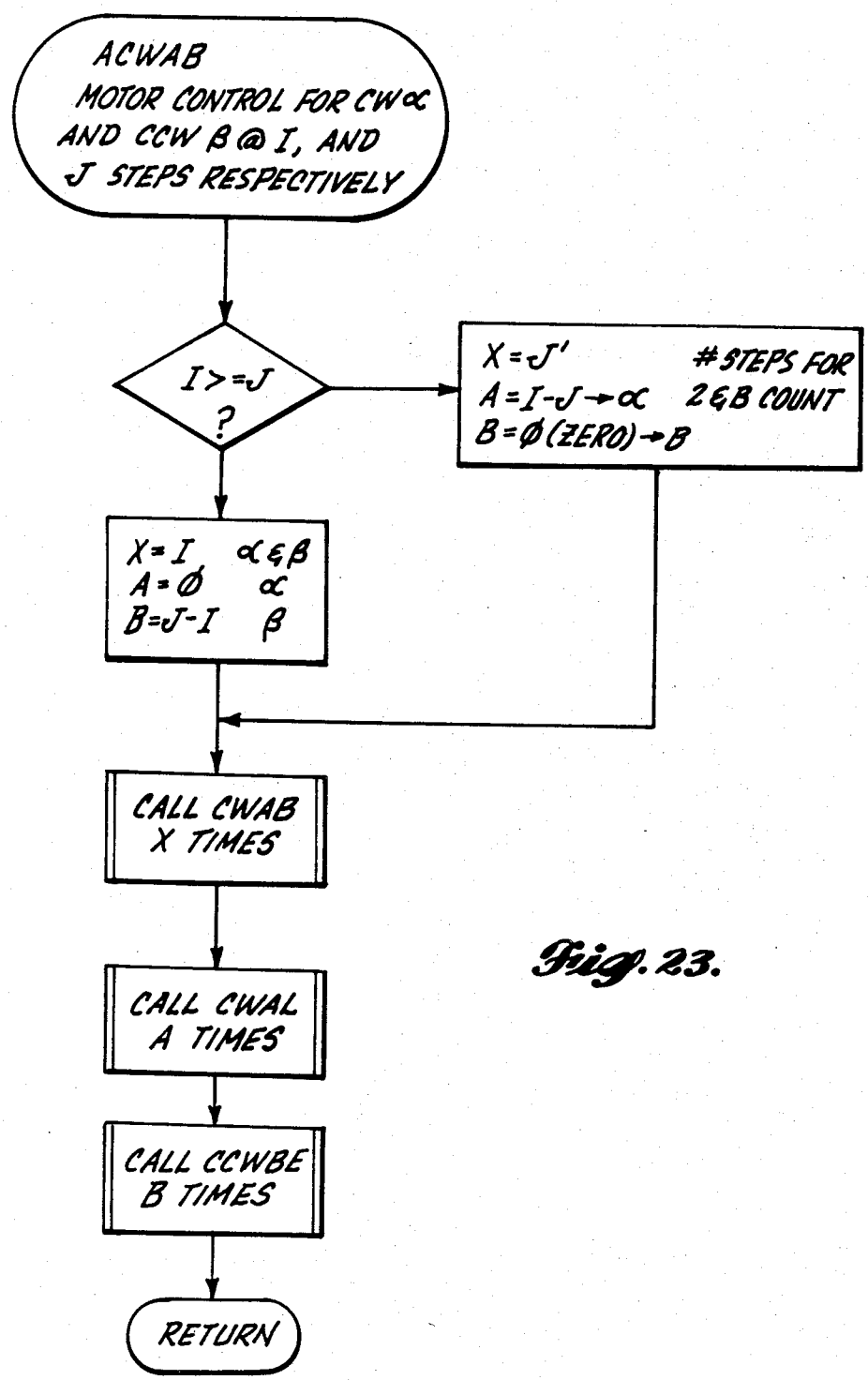
Figure 26A:
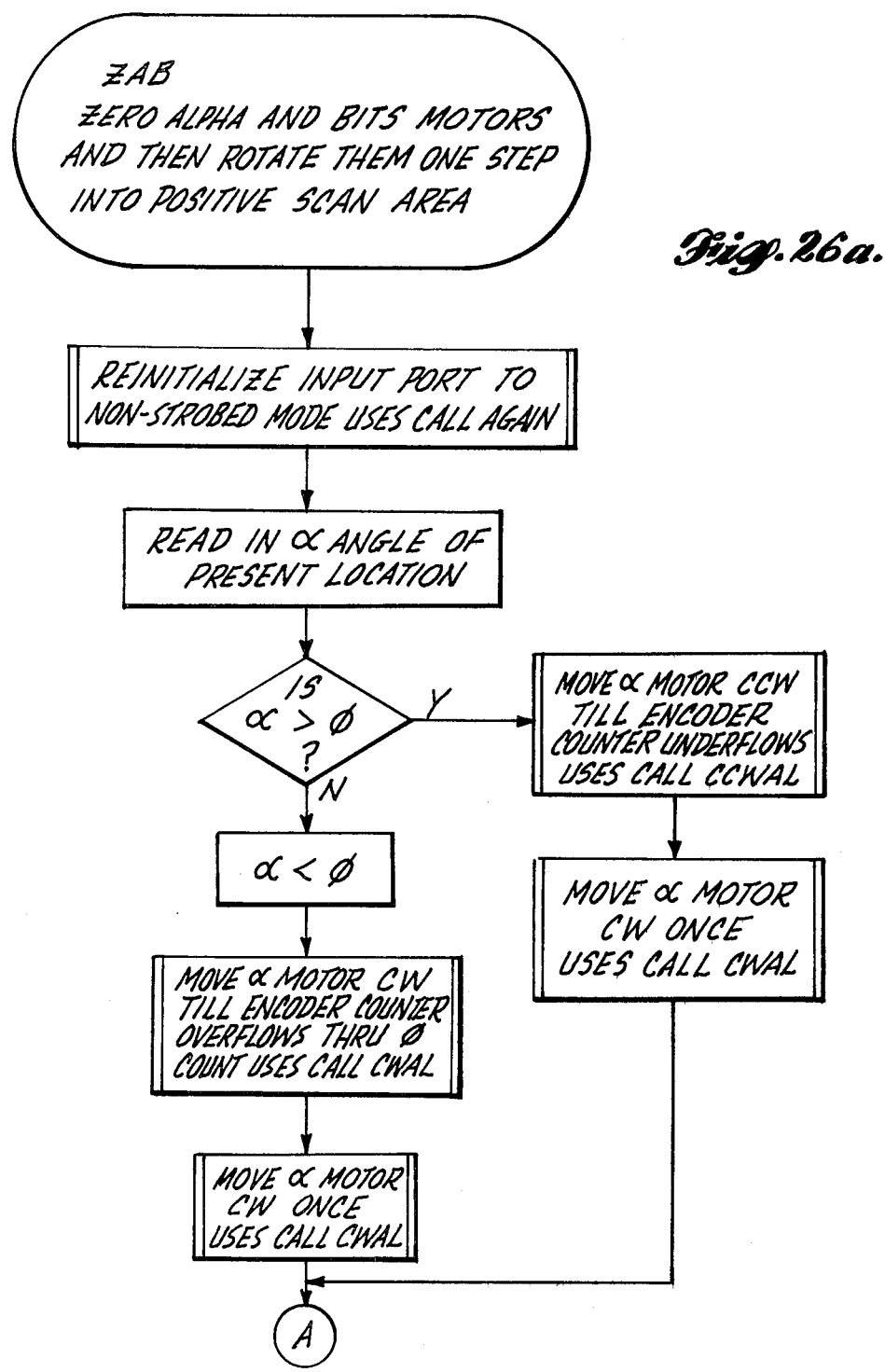
Figure 26B:
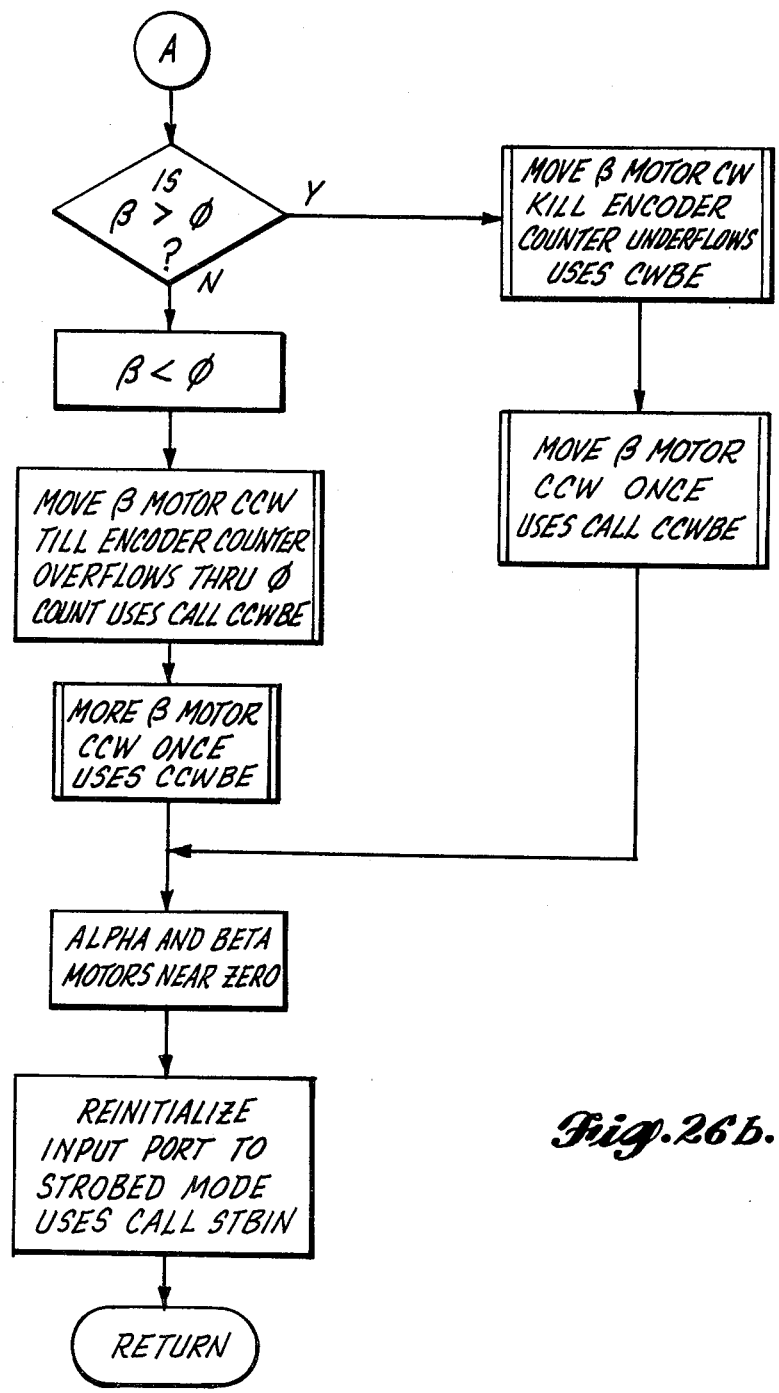

The remaining subroutines of the SMALL SCAN routine described in the lising in FIG. 19c, include ZABSUB and ZAB, the former being a transition routine, shown in detail in the flow diagram of FIG. 25, for calling up the related subroutine of ZAB shown in FIGS. 26a and 26b for zeroing the alpha and beta sensors once every 10 full cycles of the SMALL SCAN dither. With reference to FIG. 26a, ZAB requires reinitialization of the I/O ports 86 that receive the binary and coded angle values for alpha and beta so that ports 86 are in a non-strobed mode, for which purpose the subroutine ANGIN described above in FIG. 15a is called. Thereafter, the alpha angle is read and if the module 16 is in a position where alpha is greater than zero as determined by the decision operation, the alpha scan motor 22a is driven counter-clockwise until the alpha angle encoder crosses zero (underflow) and for this counter-clockwise rotation the subroutine CCWAL is called. Then, the alpha drive motor 22a advanced clockwise one step by calling CWAL once to advance the alpha scanner one step into the positive scan or testing area 14 (FIG. 2) corresponding to one positive count on the binary angle counter 74a which is responsive to alpha angle encoder 24a (see FIG. 6). If the converse is true, alpha being less than zero, then the opposite operations are effected in which the alpha drive motor 22a steps the alpha scanner clockwise until the angle counter 74a overflows through zero count by calling up CWAL the required number of steps, and then advancing the alpha stepping motor 22a one further clockwise step, again using CWAL to dispose the alpha sensor one step into the positive scan area 14.

Corresponding operations are performed on the beta sensor angle so as to dispose the beta sensor 20d one step from zero into the positive scan area 14. It is noted that the zero outputs of the alpha and beta binary angle counters (see alpha counter 74a in FIG. 6) are calibrated to be zero when the alpha and beta sensors are precisely aligned with the imaginary base lined between the axes of the sensors as indicated in FIG. 2. Now both the alpha and beta sensors 20a and 20b have been zeroed and I/O ports 86 are reinitialized to the strobed mode by calling STBIN, described above in FIG. 15a, and the flow of the program is returned to the SMALL SCAN routine for continuing with the dither phase of the SMALL SCAN routine.

While only a particular embodiment has been disclosed herein it will be readily apparent to persons skilled in the art that numerous changes and modifications can be made thereto including the use of equivalent means, devices and methods steps, without departing from the spirit of the invention.

The embodiments of the invention in which an exclusive property or privilege is claimed are defined as follows:

1. An integrated probing, probe position sensing and probe signal versus position indicating system for use in testing work pieces, comprising:
   an independently movable signal producing probe means for producing an output probe signal of variable value representing a predetermined characteristic of a workpiece;
   a spot source of radiation mounted with the said probe means for movement as a unit therewith;
   first and second directional, radiation sensor means, mounted in spaced apart relation and for movement so as to scan across said radiation source means;
   first and second angle determining means coupled to said first and second directional radiation sensor means, respectively, for producing signals representing the angles of said first and second directional radiation sensor means when they are respectively aligned with said radiation source means;
   position determining control means for receiving said signals representing said angles from said first and second angle determining means and for producing position coordinate signals representing the position coordinates of said radiation source means and hence said probe means in response to said signals representing said angles;
   signal correlating control means for receiving said probe output signal from said probe means and for receiving said position coordinate signals from said position determining control means and in response thereto correlating said output probe signal with said position coordinate signals; and,
   indicating means responsive to said signal correlating control means for indicating the correlation between said output probe signal and said position coordinate signals.

2. The system of claim 1 wherein said signal correlating control means includes memory means for storing the correlated output probe signal and position coordinate signals, and said indicating means including means for retrieving such correlated signals from said memory means of said signal correlating control means.

3. The system of claim 1 wherein said indicating means comprises video display means for displaying a video scan representation of the spatial relationship between the correlated output probe signal and position coordinate signals.

4. The system of claim 3 wherein said signal correlating control means comprises memory means for storing the correlated output probe signal and position coordinate signals in a predetermined memory-mapped format in which variations in the probes output signal are retrievable in a sequence corresponding to the presentation of such signal variations on such video display.

5. The system of claim 3 wherein said video display means comprises a CRT and associated control means for generating a visual representation of variations in the level of said output probe signal as a function of the position of said probe means on a workpiece surface such that a screen of said CRT presents a two-dimensional field of such probe signal variations as a function of probe position in which said two-dimensional field corresponds to a probing area on the surface of a workpiece.

6. The system of claim 5 wherein said control means of said CRT generates a predetermined video background on said screen representing the absence of a probe output signal above a predetermined minimum level threshold at a particular workpiece position or positions, and means for generating a first video level different from said video background in response to a level of said probe output signal that exceeds such predetermined minimum level threshold to thereby differentiate on the screen of said CRT those represented areas of a workpiece surface that have been probed by said probe means and those areas that have not been probed by said probe means.

7. The system of claim 1 wherein said signal correlating control means comprises means for quantizing the level of said probe output signal into at least two different, discrete levels.

8. The system of claim 1 further comprising a portable sensor support means including detachable mounting means for detachably mounting said support means to a surface of a workpiece adjacent an area that is to be probed, and said first and second directional radiation sensor means being mounted on said support means in said spaced apart relation.

9. The system of claim 8 wherein said support means comprises an elongate support member and said first and second directional radiation sensor means are mounted adjacent opposite ends of said member.

10. The system of claim 9 wherein said detachable mounting means of said support means comprise means affixed to said support member for detachable mounting to a surface of a workpiece.

11. The system of claim 9 wherein said first and second angle determining means are respectively mounted along with said first and second directional sensor means on said support means.

12. The system of claim 1 wherein at least said first directional radiation sensor means comprises a scanning head mounted for scanning movement and having a slotted body defining a radiation transmissive slot and further having a trandsducer means responsive to said radiation to produce an electrical signal, said transducer means being mounted on said body adjacent said slot so that said slot is alignable with said source of radiation to channel said radiation to said transducer means when so aligned.

13. The system of claim 1 wherein said probe means is a nondestructive testing probe comprising a probe support body and a probe transducer mounted on said support body for producing said output probe signal, and said radiation source means is mounted on said support body.

14. The system of claim 11 wherein said probe body is sized, shaped and weighted for being manually guided over a workpiece surface.

15. The system of claim 14 wherein said support body of said probe means has a vertically elongated shape in which the lower end thereof is engageable with a surface of a workpiece for disposing said transducer in probing communication with such workpiece surface and has an upper end elevated above the surface of such workpiece on which said radiation source means is mounted.

16. The system of claim 15 wherein said radiation source means comprises a radiation emissive solid state device.

17. An integrated test probing, probe position monitoring and probe signal versus position displaying method, comprising the steps of:
moving a test probe relative to a workpiece to produce a variable level test signal representing a predetermined characteristic of such workpiece at the probe position;
producing position indicating radiation at the probe which radiates to distant sensors;
scanning first and second separated radiation sensors across a scanning field in which the test probe is located;
determining the scan angles of the sensors at which they detect radiation from said test probe;
determining position coordinates of the test probe in said field from said scan angles;
correlating level variations of said test probe signal with said position coordinates; and
displaying the correlated level variations of said test probe signal and said position coordinates.

* * * * *